United States Patent
LaBelle et al.

(10) Patent No.: US 10,939,857 B2
(45) Date of Patent: Mar. 9, 2021

(54) THREE-DIMENSIONALLY PRINTED BLOOD GLUCOSE SENSING DEVICE AND FABRICATION METHOD

(71) Applicant: Arizona Board of Regents on behalf of Arizona State University, Scottsdale, AZ (US)

(72) Inventors: Jeffrey LaBelle, Tempe, AZ (US); Anngela Adams, Phoenix, AZ (US); Garrett Repp, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 200 days.

(21) Appl. No.: 16/011,796

(22) Filed: Jun. 19, 2018

(65) Prior Publication Data

US 2019/0046092 A1    Feb. 14, 2019

Related U.S. Application Data

(60) Provisional application No. 62/523,426, filed on Jun. 22, 2017.

(51) Int. Cl.
*A61B 5/1486* (2006.01)
*C12Q 1/00* (2006.01)
(Continued)

(52) U.S. Cl.
CPC ........ *A61B 5/1486* (2013.01); *A61B 5/14532* (2013.01); *A61B 5/150358* (2013.01);
(Continued)

(58) Field of Classification Search
CPC ......... A61B 5/1486; A61B 5/145; A61B 5/00; A61B 5/14532; A61B 5/150358;
(Continued)

(56) References Cited

U.S. PATENT DOCUMENTS

| 8,815,178 B2 | 8/2014 | Bishop et al. |
| 10,386,321 B2 | 8/2019 | LaBelle et al. |

(Continued)

FOREIGN PATENT DOCUMENTS

| WO | 2010111484 A1 | 9/2010 |
| WO | 2012009322 A1 | 1/2012 |

(Continued)

OTHER PUBLICATIONS

Hye-Young Chang & Zun-Ung Bae* (1997) Adenosine-Modified Electrodes for the Determination of Glucose Without Using an Immobilized Redox Mediator, Analytical Letters, 30:11, 1981-1992, DOI: 10.1080/00032719708001714, abstract only. (Year: 1997).*

(Continued)

*Primary Examiner* — Christine T Mui
(74) *Attorney, Agent, or Firm* — Withrow & Terranova, P.L.L.C.

(57) ABSTRACT

A blood glucose sensing device includes a substrate, multiple three-dimensionally (3D) printed electrode leads comprising graphene arranged on or over the substrate, and glucose monitoring chemistry arranged in or on (e.g., adsorbed in) at least one of the 3D printed electrode leads. An end portion of a counter electrode lead may partially surround an end portion of a working electrode lead, and a reference lead may be further provided, Optionally, the 3D printed electrode leads may include a thermoplastic material, such as an aliphatic polyester. The glucose monitoring chemistry may include an enzyme.

25 Claims, 29 Drawing Sheets

(51) Int. Cl.
G01N 27/327 (2006.01)
G01N 33/66 (2006.01)
A61B 5/145 (2006.01)
A61B 5/15 (2006.01)
A61B 5/00 (2006.01)
A61B 5/157 (2006.01)
A61B 5/1495 (2006.01)
G01N 33/49 (2006.01)

(52) U.S. Cl.
CPC ............ *A61B 5/4839* (2013.01); *C12Q 1/006* (2013.01); *G01N 27/3271* (2013.01); *G01N 33/66* (2013.01); *A61B 5/1495* (2013.01); *A61B 5/157* (2013.01); *A61B 5/6826* (2013.01); *A61B 2562/0295* (2013.01); *G01N 33/49* (2013.01)

(58) Field of Classification Search
CPC .... A61B 5/150007; A61B 5/15; C12Q 1/006; C12Q 1/004; C12Q 1/001; C12Q 1/00; G01N 27/3271; G01N 27/327; G01N 27/30; G01N 27/28; G01N 27/26
USPC ...................................... 436/95; 422/500, 50
See application file for complete search history.

(56) References Cited

U.S. PATENT DOCUMENTS

| | | |
|---|---|---|
| 2013/0183243 A1 | 7/2013 | LaBelle et al. |
| 2017/0202691 A1 | 7/2017 | LaBelle et al. |
| 2019/0024131 A1 | 1/2019 | LaBelle et al. |
| 2019/0150815 A1 | 5/2019 | LaBelle et al. |

FOREIGN PATENT DOCUMENTS

| | | | |
|---|---|---|---|
| WO | 2015183893 | A1 | 12/2015 |
| WO | 2017132565 | A1 | 8/2017 |
| WO | 2018148236 | A1 | 8/2018 |
| WO | 2018175448 | A1 | 9/2018 |
| WO | 2019178588 | A1 | 9/2019 |

OTHER PUBLICATIONS

Taleat, Screen-printed electrodes for biosensing: a review (2008-2013), Microchim Acta, 2014, 181, 865-891. (Year: 2014).*
La Belle, Self-monitoring of tear glucose: the development of a tear based glucose sensor as an alternative to self-monitoring of blood glucose, Chem. Commun., 2016, 52, 9197-9204. (Year: 2016).*
U.S. Appl. No. 16/543,400, filed Feb. 10, 2017.
U.S. Appl. No. 16/495,682, filed Sep. 19, 2019.
U.S. Appl. No. 16/482,661, filed Jul. 31, 2019.

Adams, A., "3D Printed Glucose Monitoring Sensor," A Thesis Presented in Partial Fulfillment of the Requirements for the Degree Master of Science, May 2017, Arizona State University, 50 pages.
Author Unknown, "Accessories," CH Instruments, Inc., Retrieved Jun. 12, 2017 from http://www.chinstruments.com/accessories.shtml, 4 pages.
Author Unknown, "ET077-40 Zensor TE100 SPEs—Pack of 40," eDAQ, Retrieved Jun. 14, 2017 from https://www.edaq.com/ET077-40, 3 pages.
Author Unknown, "Screen-Printed Electrode," CH Instruments, Inc., Retrieved Jun. 12, 2017 from https://www.chinstruments.com/accessory_pdf/Printed%20Electrodes.pdf, 2 pages.
Author Unknown, "Zensor Screen Printed Electrodes," Nanoshel, Retrieved Jun. 14, 2017 from https://www.nanoshel.com/product/zensor-screen-printed-electrodes/#, 3 pages.
Bak, D., "Rapid prototyping or rapid production? 3D printing processes move industry towards the latter," Assembly Automation, vol. 23, Issue 4, Dec. 2003, MC UP Limited, pp. 340-345.
Clark, L. et al., "Electrode Systems for Continuous Monitoring in Cardiovascular Surgery," Annals of the New York Academy of Sciences, vol. 102, 1962, John Wiley and Sons, pp. 29-45.
Clarke, W. et al., "Evaluating Clinical Accuracy of Systems for Self-Monitoring of Blood Glucose," Diabetes Care, vol. 10, Issue 5, Sep. 1987, pp. 622-628.
Ferri, S. et al., "Review of Glucose Oxidases and Glucose Dehydrogenases: A Bird's Eye View of Glucose Sensing Enzymes," Journal of Diabetes Science and Technology, vol. 5, Issue 5, Sep. 2011, Sage, pp. 1068-1076.
Karyakin, A. et al., "Prussian Blue-Based First-Generation Biosensor—A Sensitive Amperometric Electrode for Glucose," Analytical Chemistry, vol. 67, Issue 14, 1995, pp. 2419-2423.
Komkova, M. et al., "Supporting Information: Noiseless performance of Prussian Blue based (bio)sensors through power generation," Retrieved Jun. 16, 2017 from https://pubs.acs.org/doi/abs/10.1021/acs.analchem.7b01142, 6 pages.
Malkoc, A. et al., "Electrochemical-Nucleic Acid Detection with Enhanced Specificity and Sensitivity," Journal of Biosensors & Bioelectronics, vol. 6, Issue 2, Jun. 2015, 5 pages.
Rengier, F. et al., "3D printing based on imaging data: review of medical applications," International Journal of Computer Assisted Radiology and Surgery, vol. 5, Issue 4, Jul. 2010, Springer, pp. 335-341.
Ventola, C. et al., "Medical Applications for 3D Printing: Current and Projected Uses," Pharmacy & Therapeutics (P&T), vol. 39, No. 10, Oct. 2014, pp. 704-711.
Yamashita, Y. et al, "'Direct electron transfer type disposable sensor strip for glucose sensingemploying an engineered FAD glucose dehydrogenase,'" Enzyme and Microbial Technology, vol. 52, 2013, Elsevier Inc., 6 pages.
Yoo, E et al., "Glucose Biosensors: An Overview of Use in Clinical Practice," Sensors, vol. 10, 2010, pp. 4558-4576.

* cited by examiner

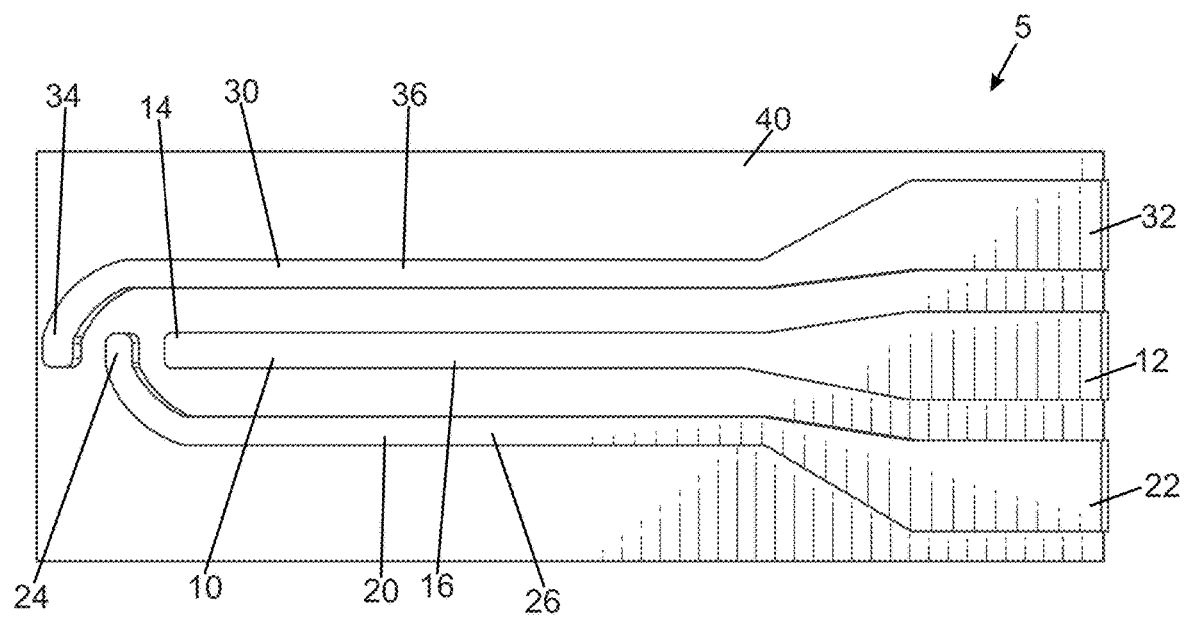
FIG._1
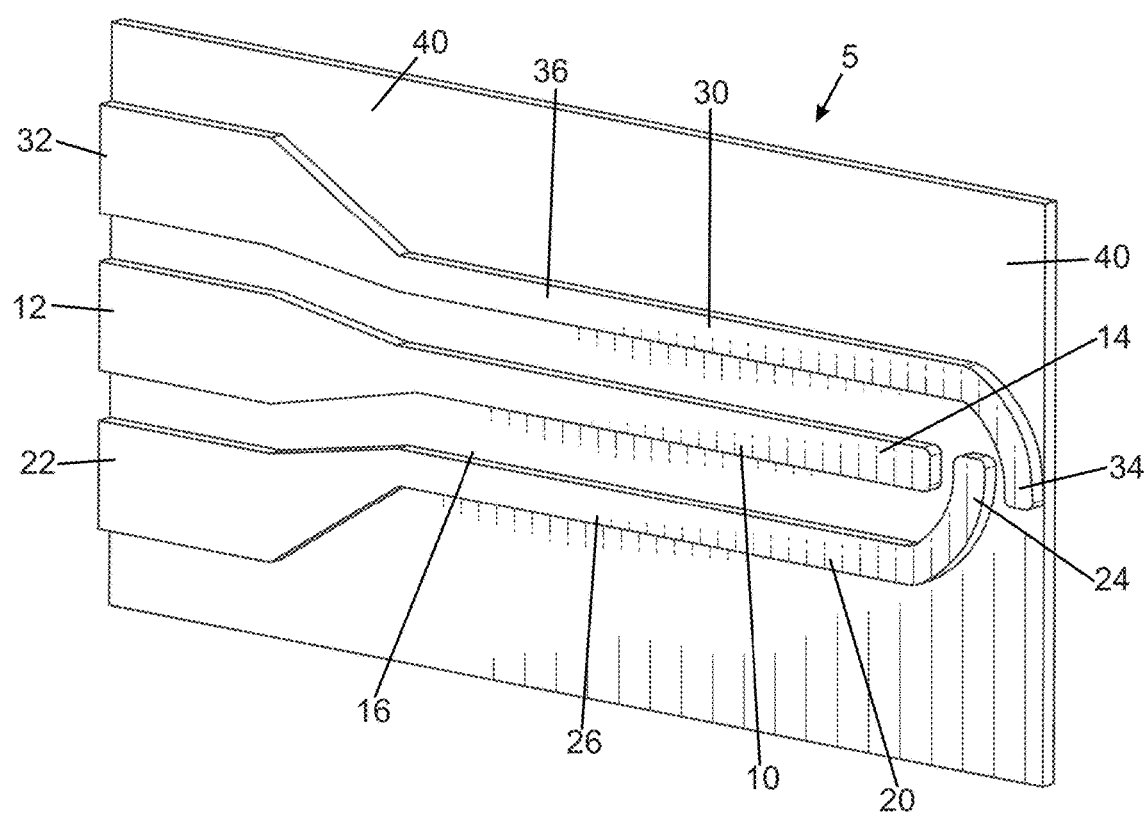
FIG._2

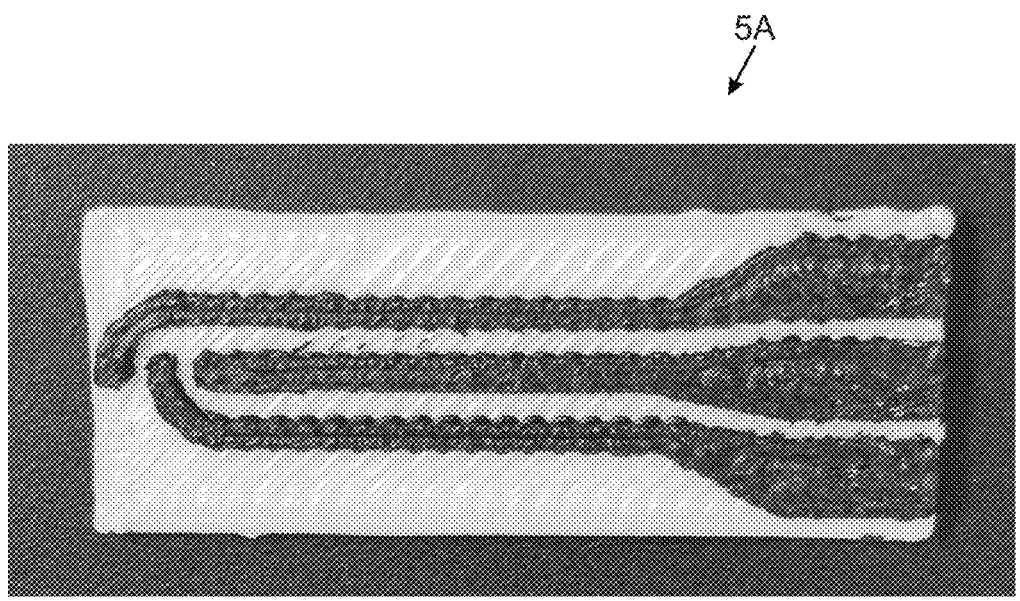
FIG._3
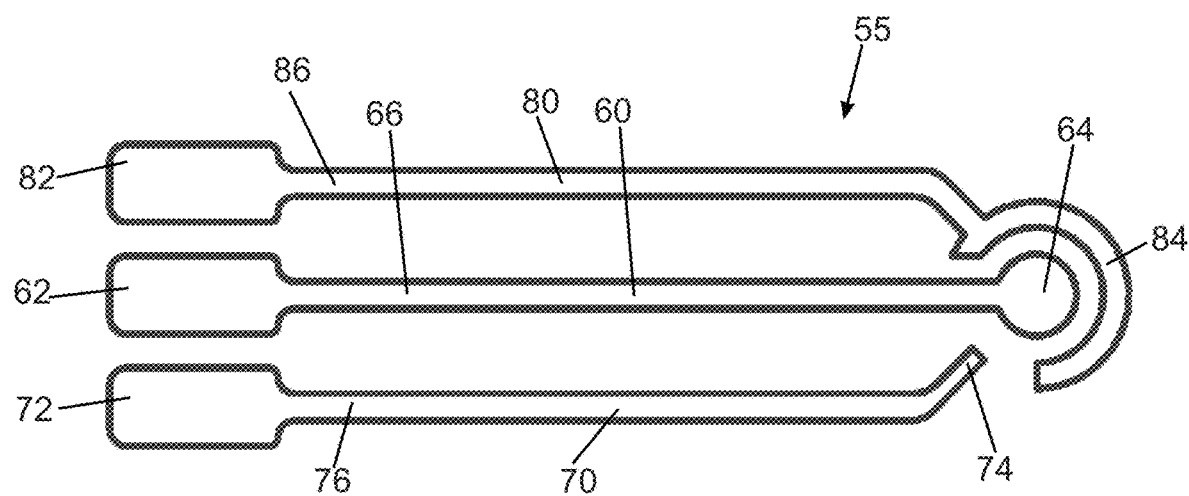
FIG._4

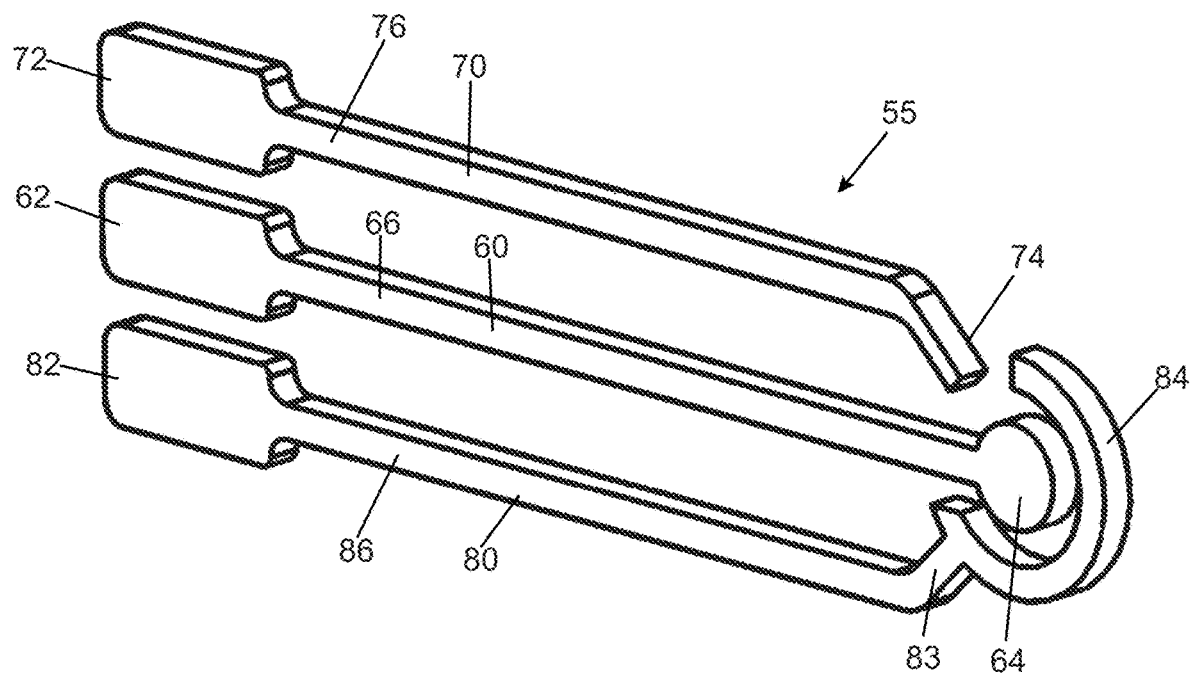
*FIG._5A*
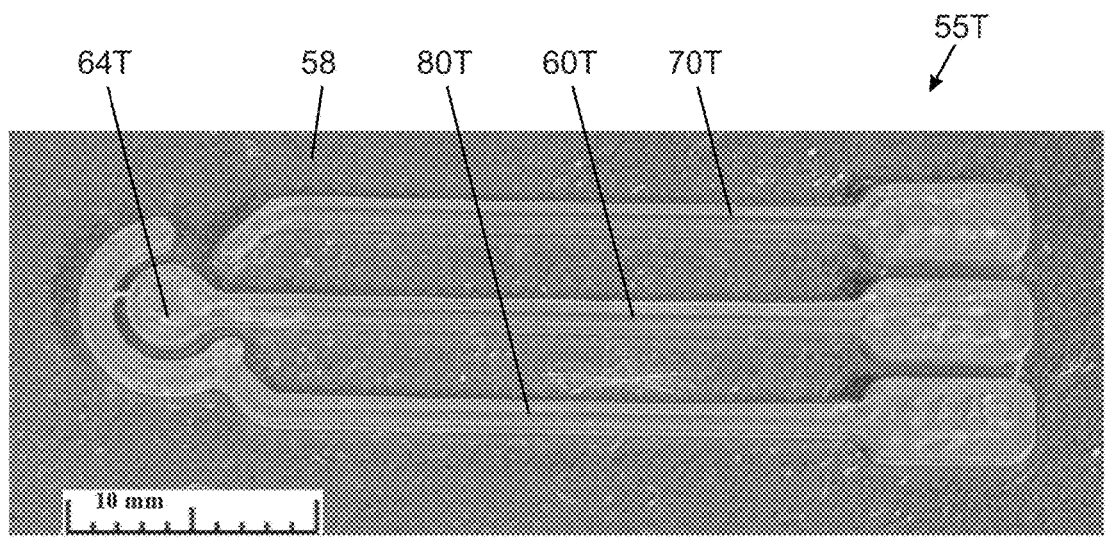
*FIG._6*

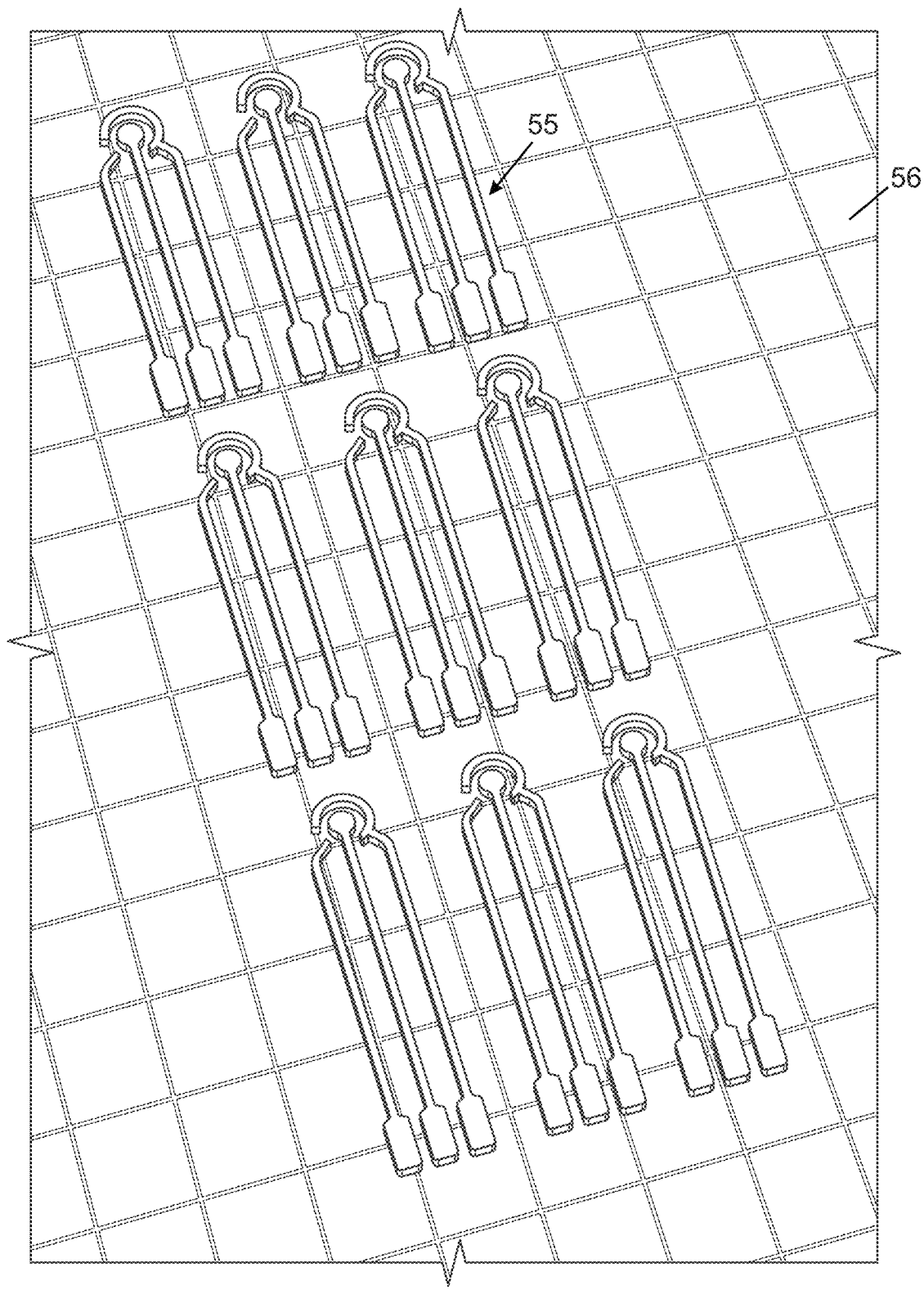
FIG._5B

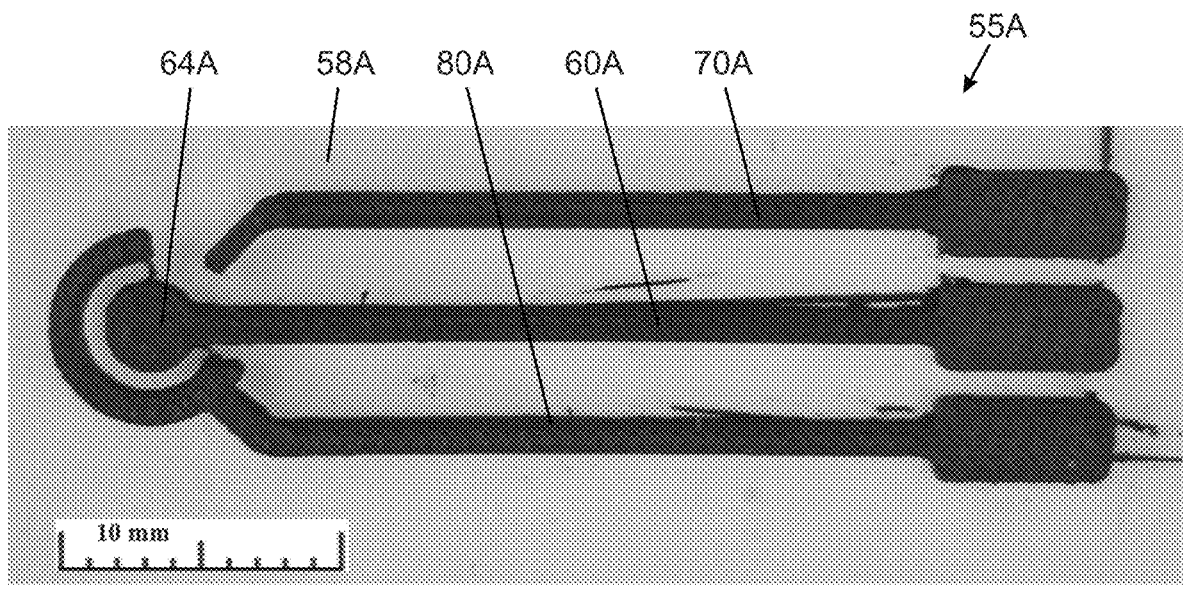
FIG._7
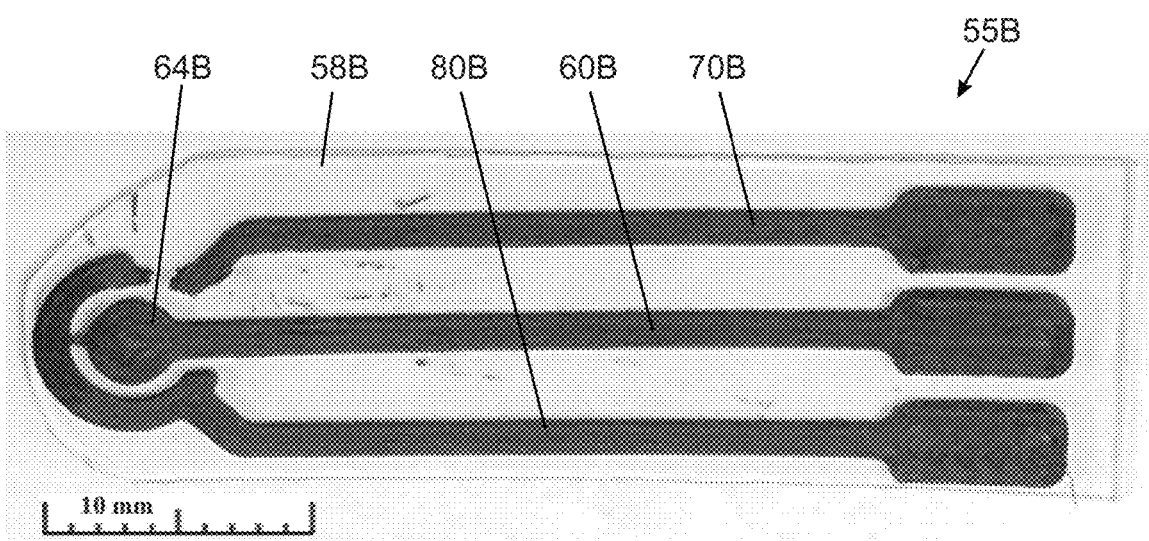
FIG._8

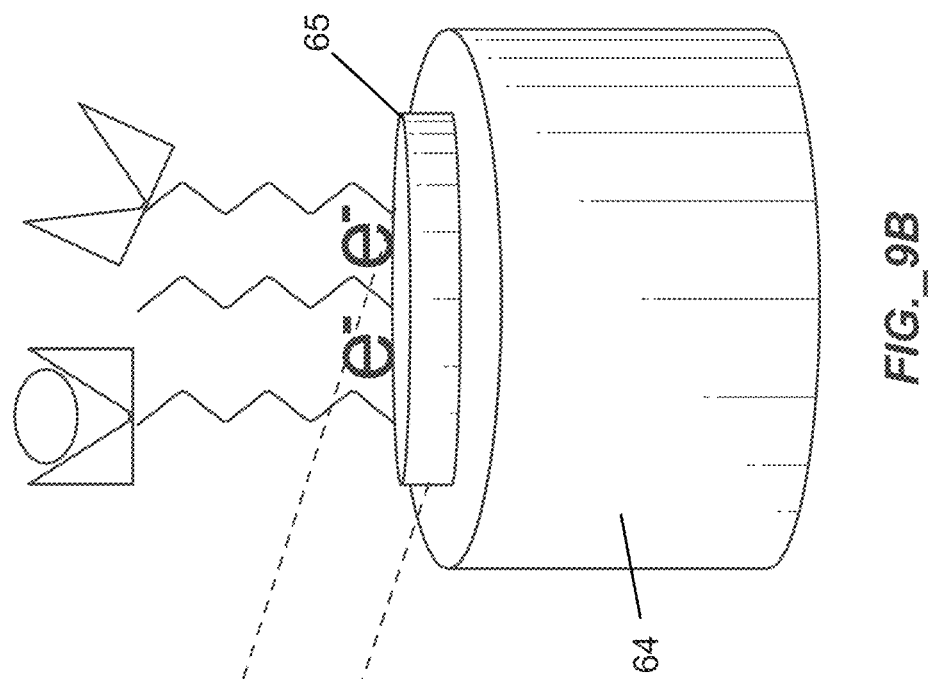
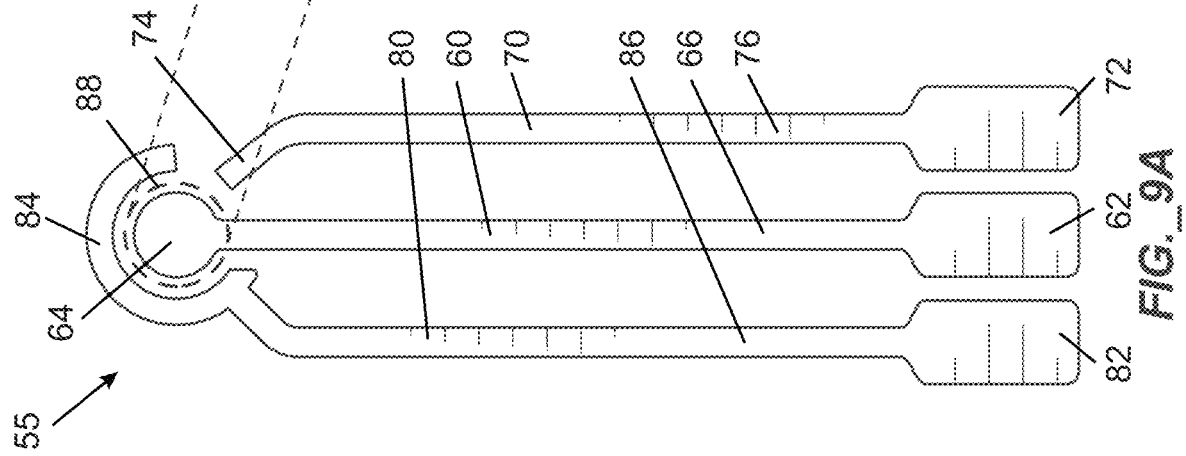
FIG._9A
FIG._9B

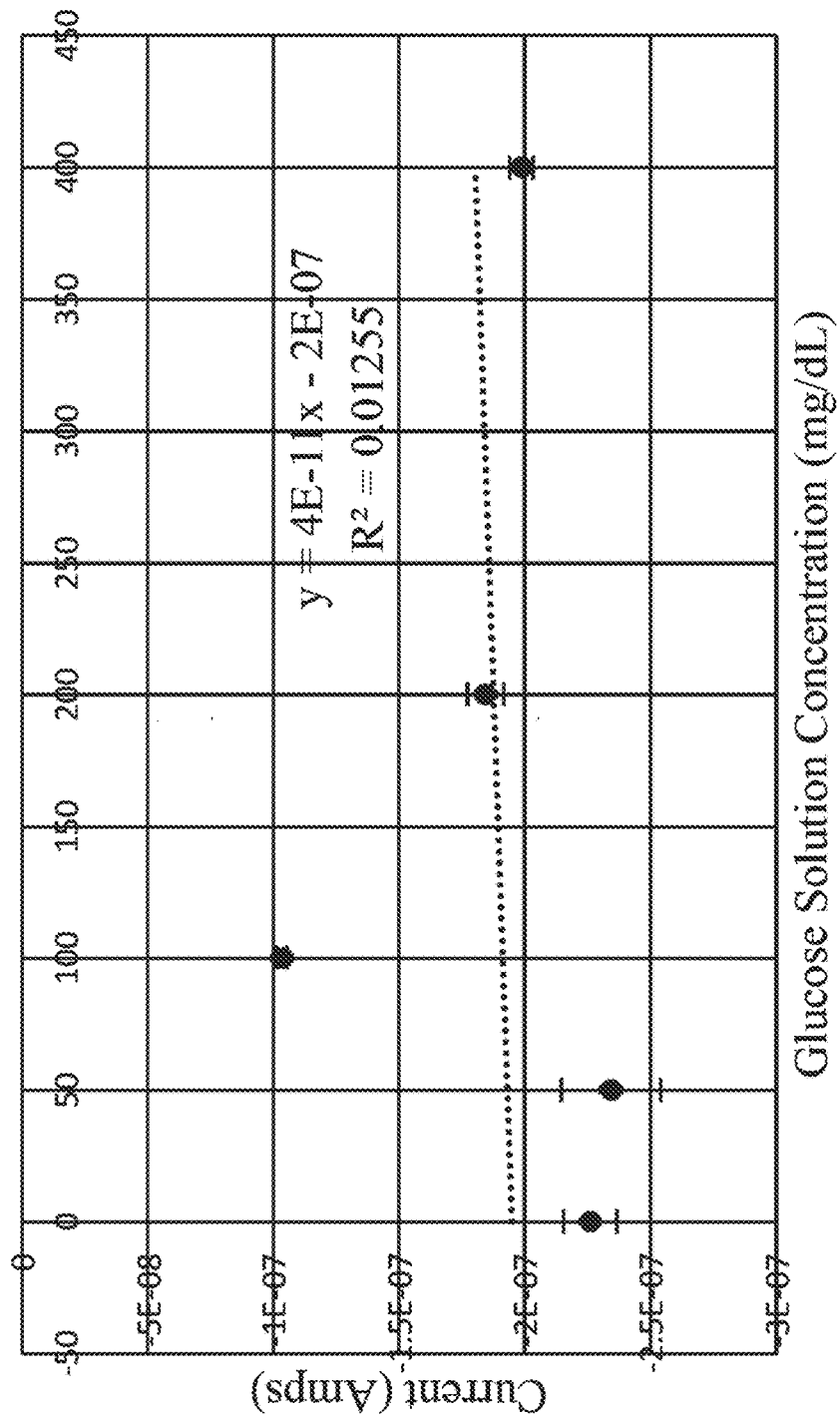
FIG_10

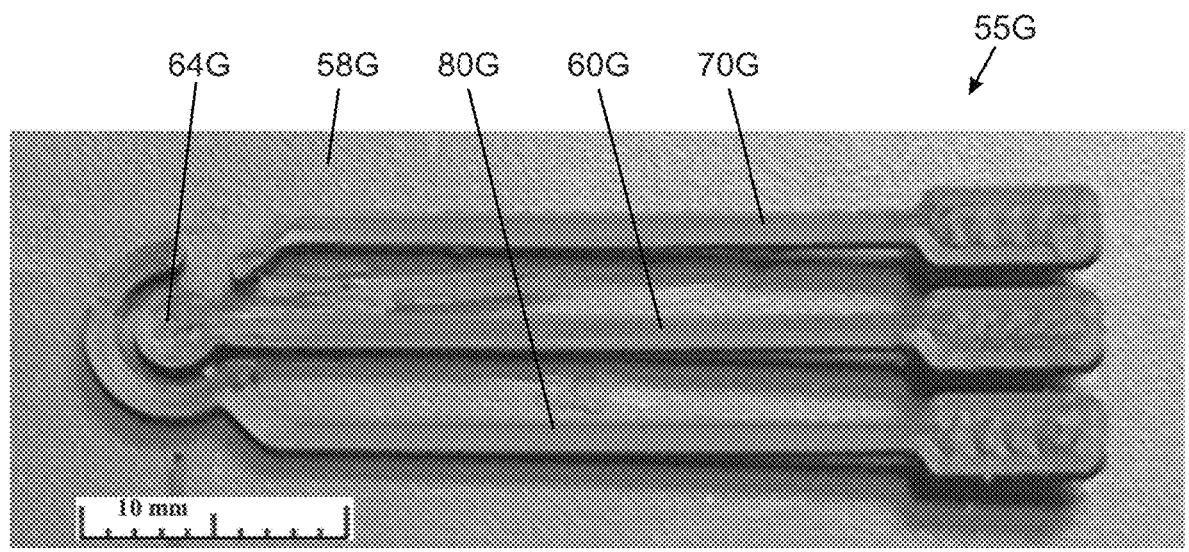
FIG._11
FIG._12

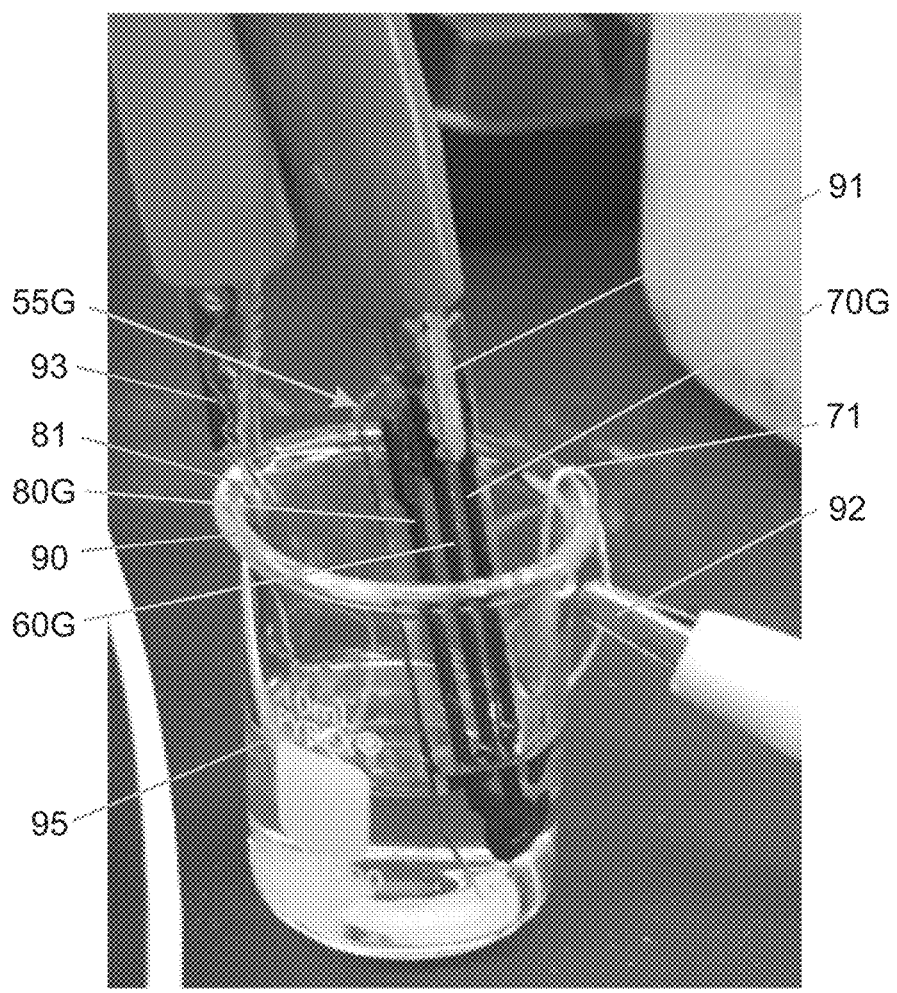
*FIG._14*
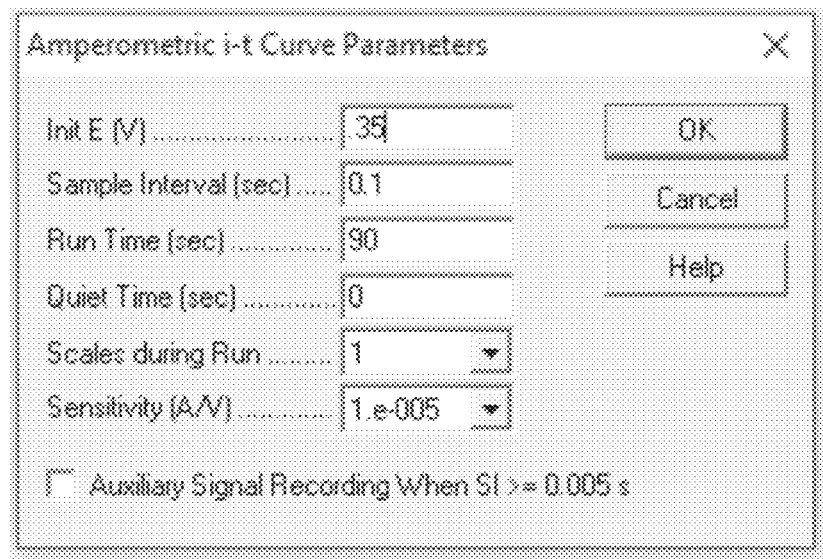
*FIG._15*

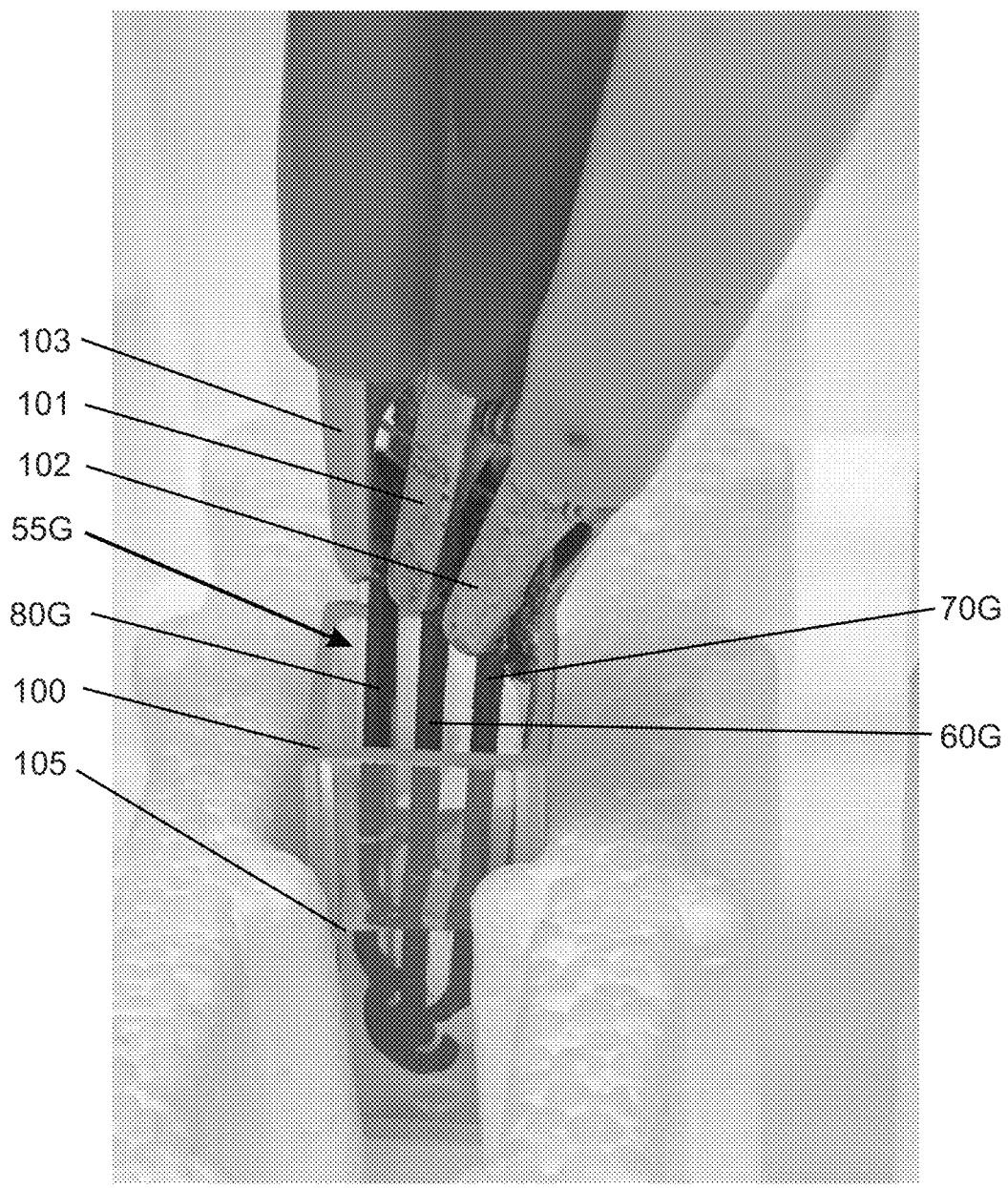
FIG._16

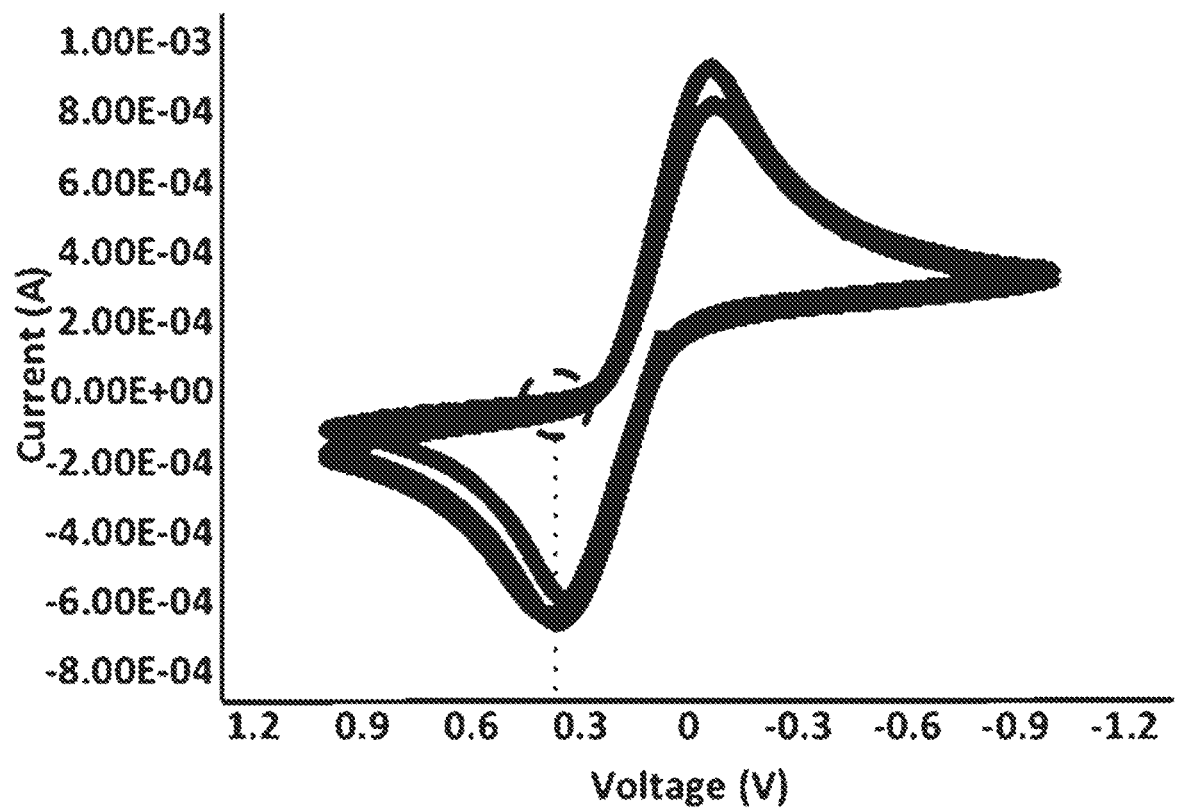
FIG._17

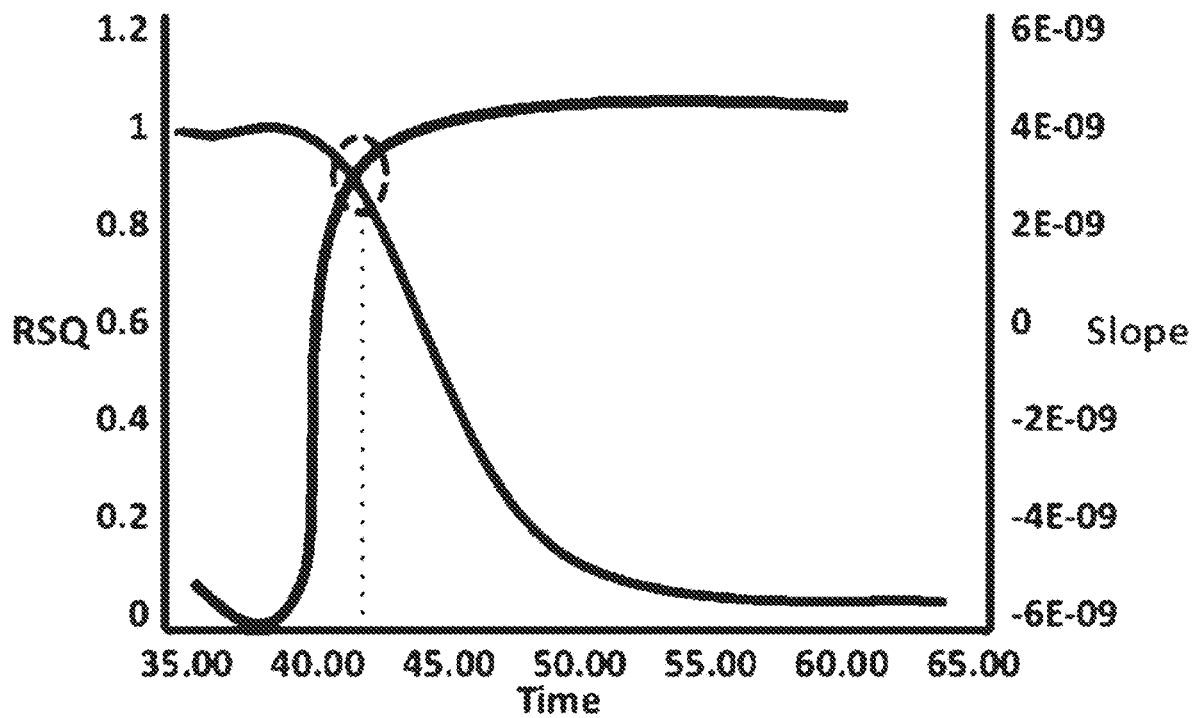
FIG._18
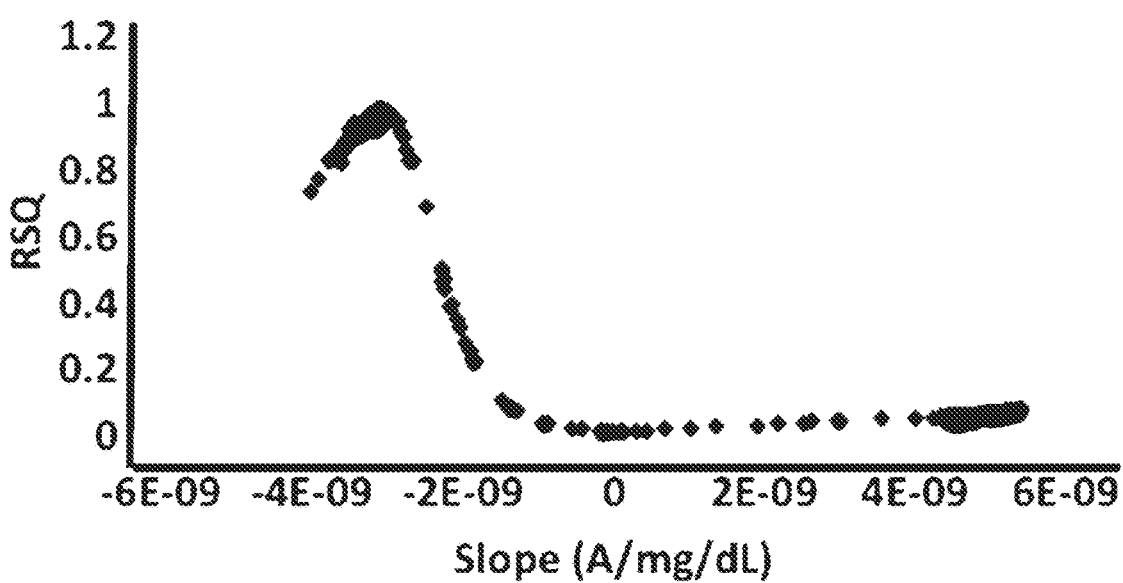
FIG._19

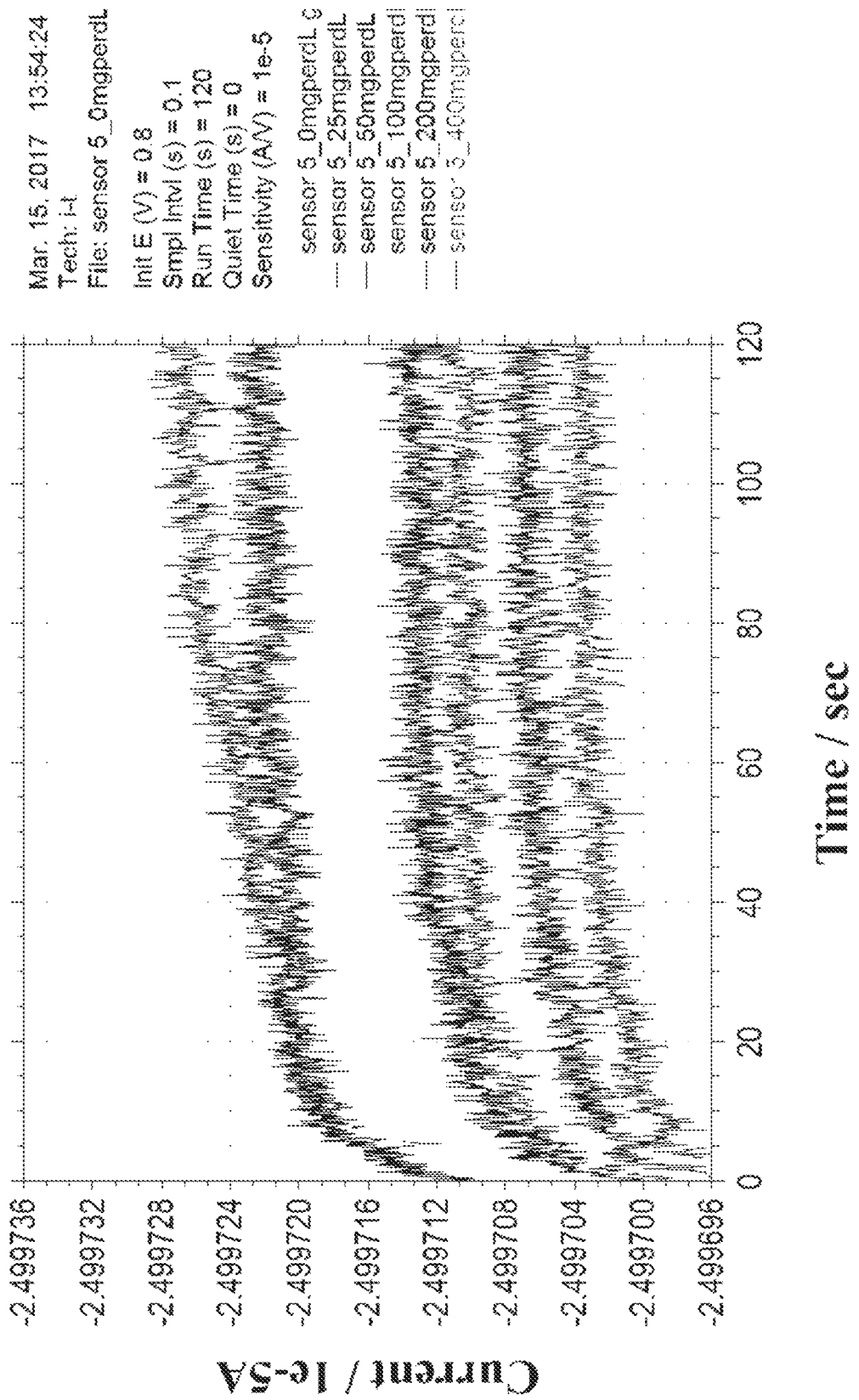
FIG_20

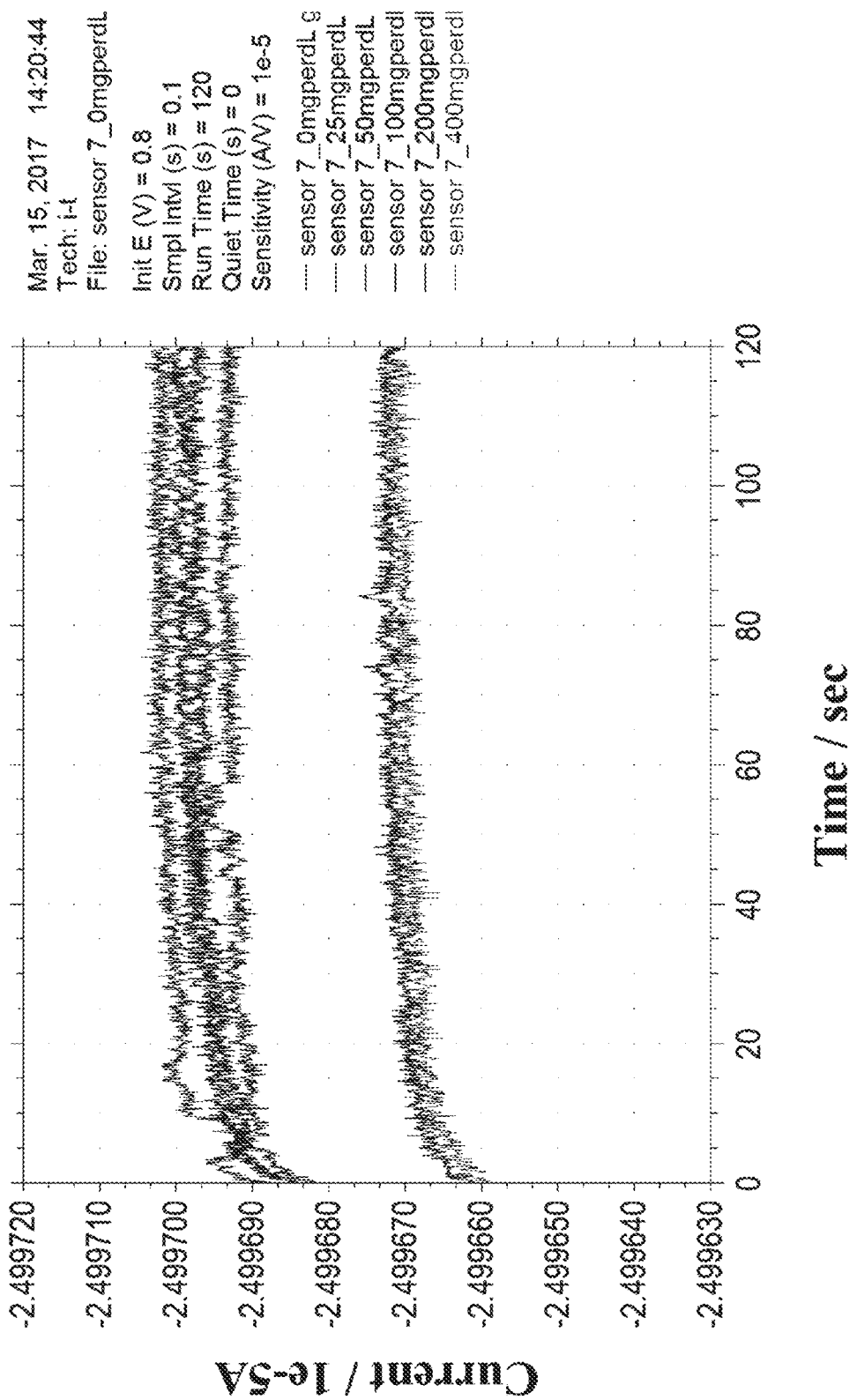
FIG_21

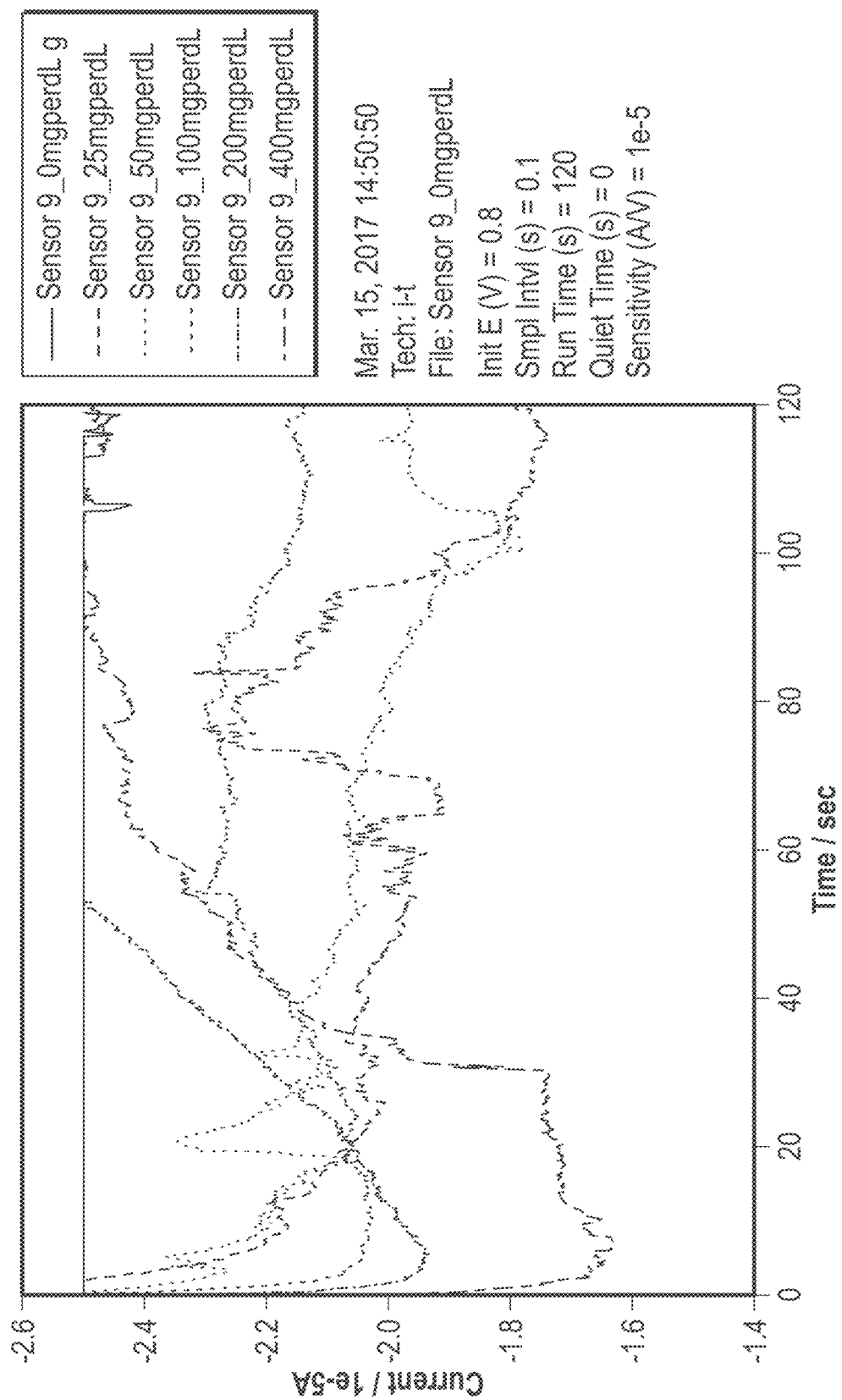
FIG._22

FIG._24

FIG_26

FIG_27

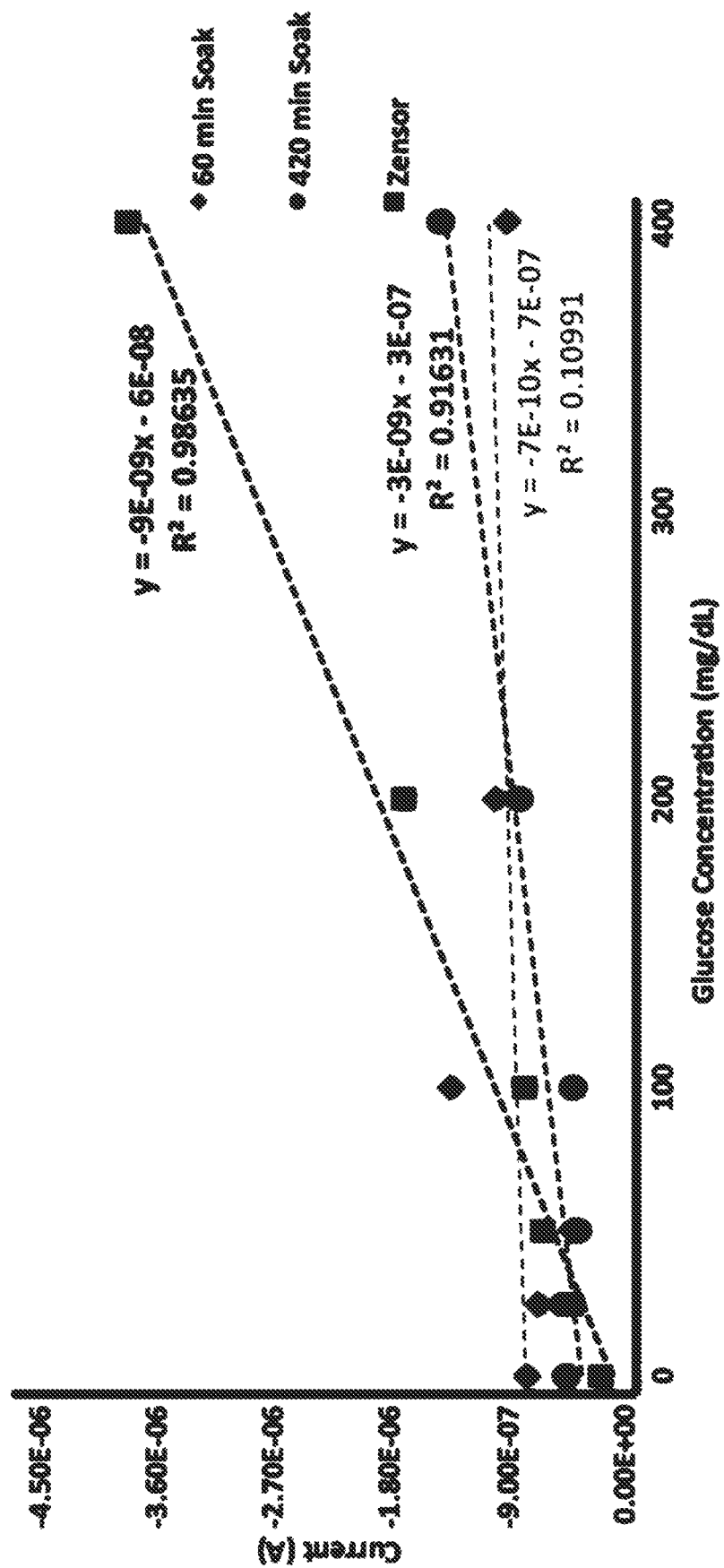
FIG._29

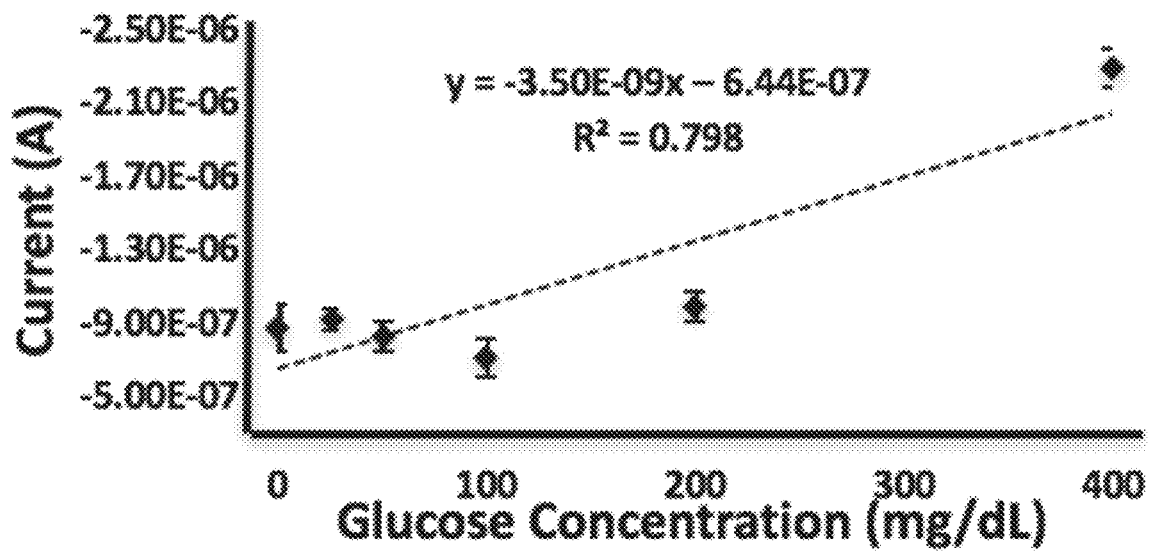
FIG._30
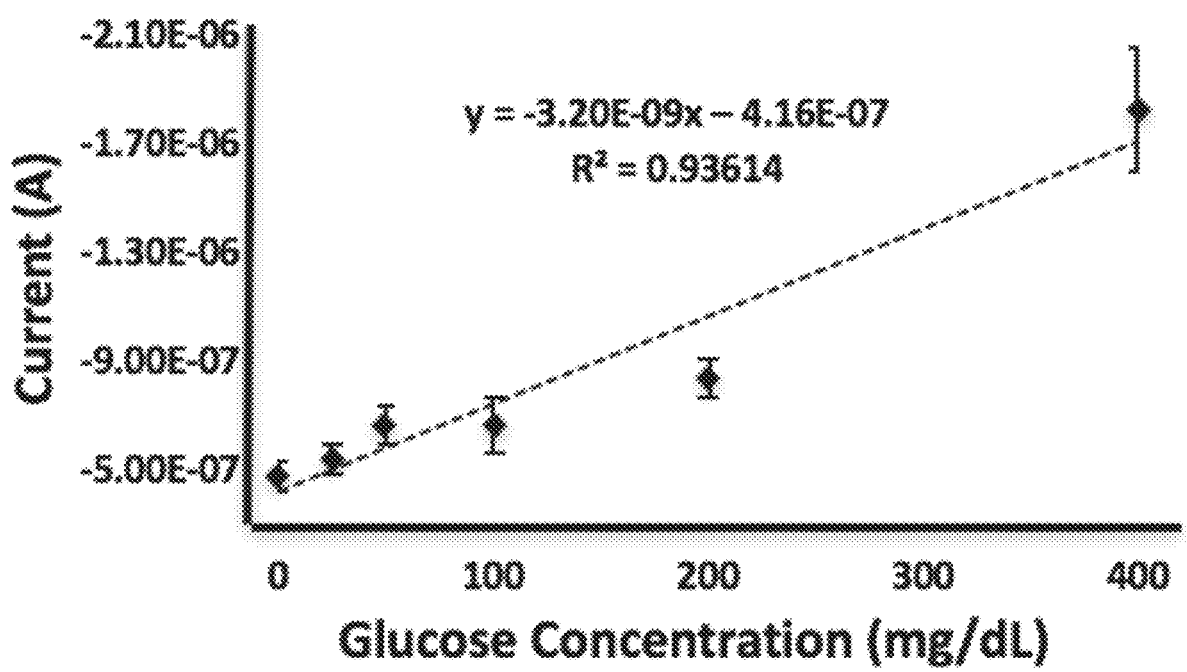
FIG._31

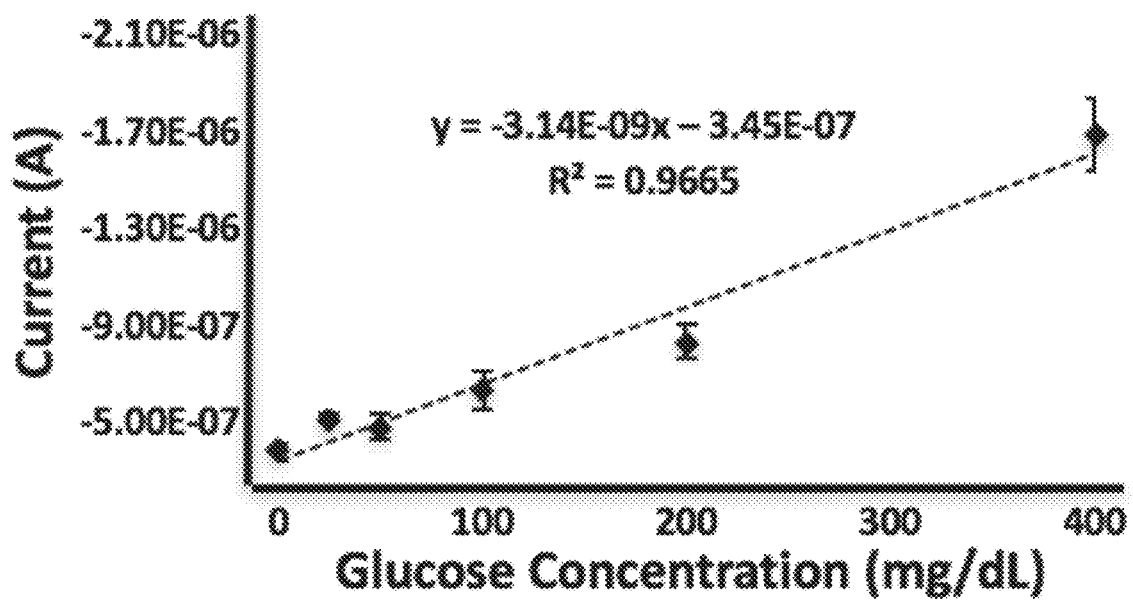
FIG._32
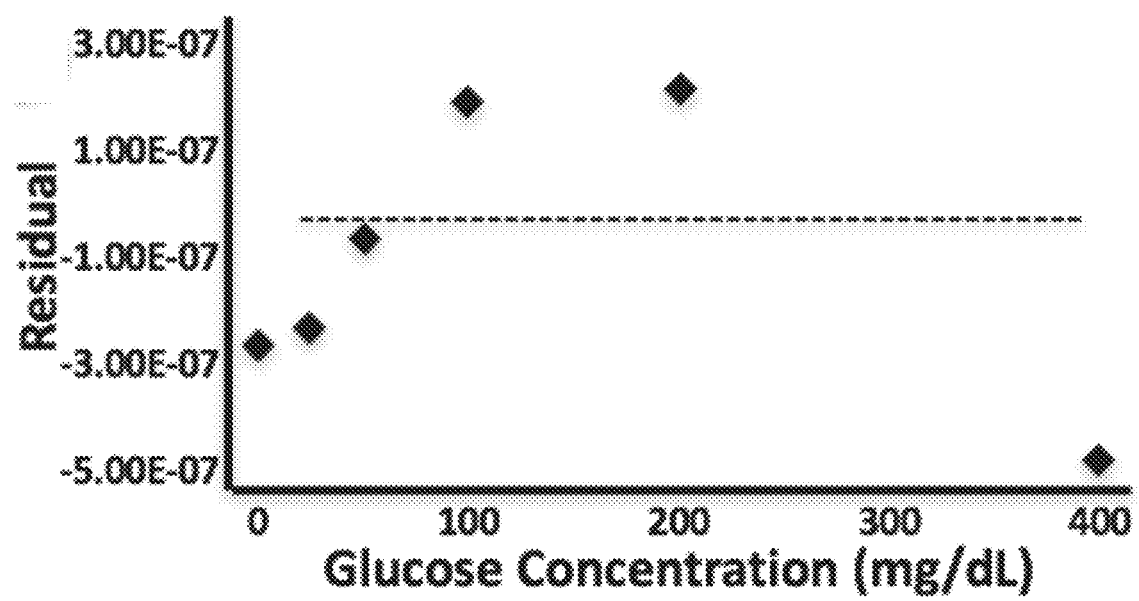
FIG._33

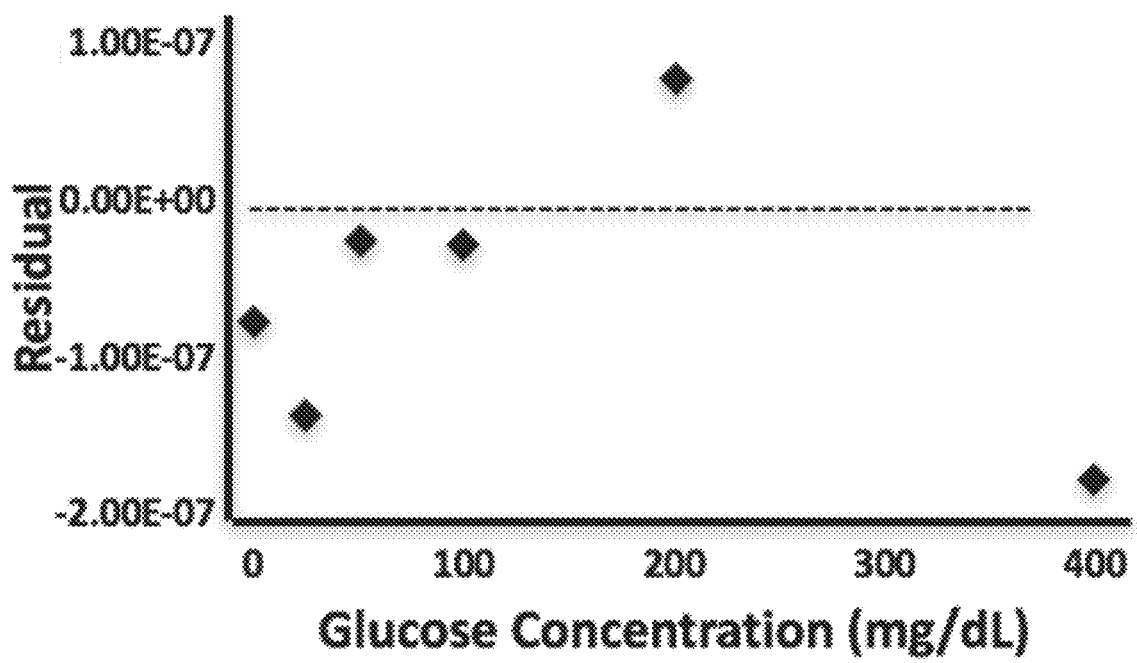
FIG._34
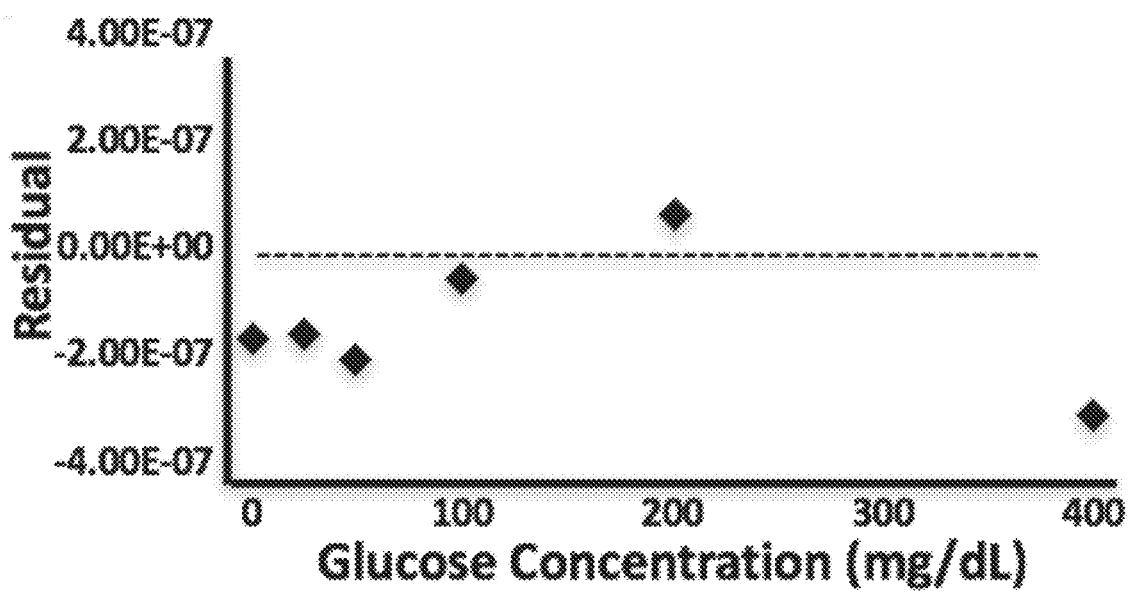
FIG._35

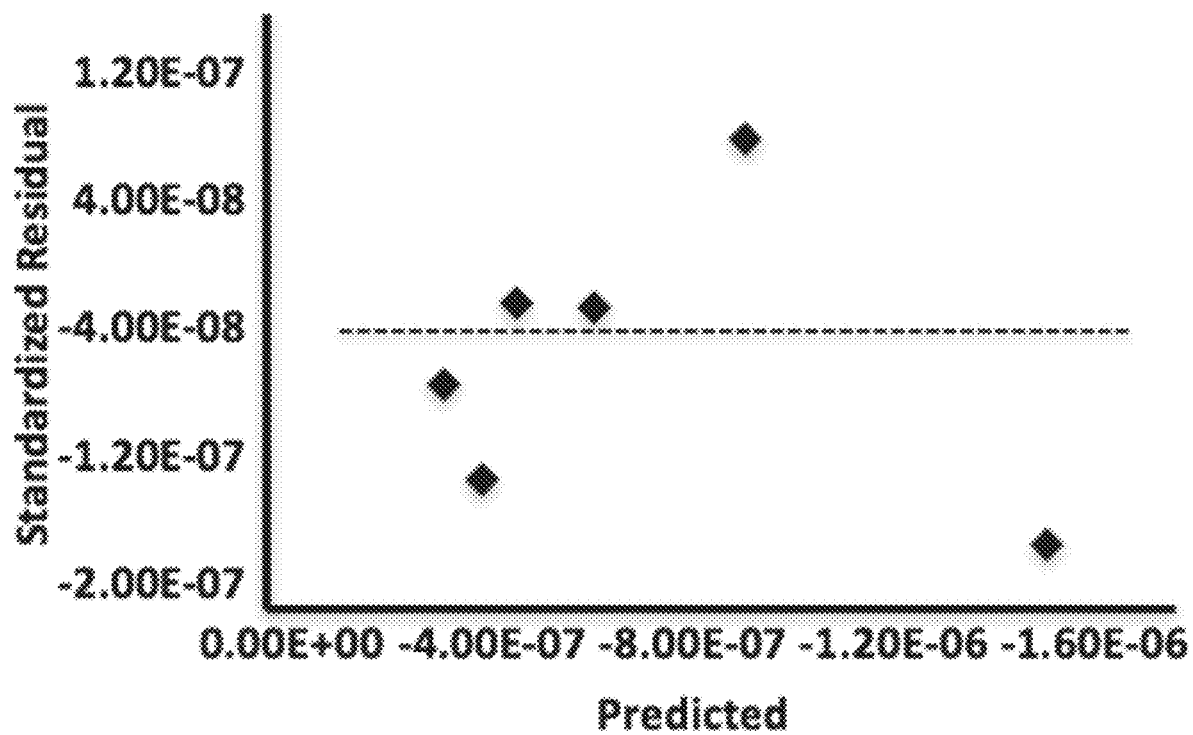
FIG._38
| Material | Cost Per Test Strip |
|---|---|
| Conductive Graphene PLA Filament | $0.05 |
| Mylar Substrate | $0.06 |
| GDH Enzyme | $0.18 |
| PBS | $0.05 |
| Ferricyanide | $0.06 |
| Total: | $0.40 |
FIG._39

THREE-DIMENSIONALLY PRINTED BLOOD GLUCOSE SENSING DEVICE AND FABRICATION METHOD

STATEMENT OF RELATED APPLICATION(S)

This application claims priority to U.S. Provisional Patent Application No. 62/523,426 filed on Jun. 22, 2017, with the foregoing application hereby being incorporated by reference herein.

TECHNICAL FIELD

This disclosure relates to blood glucose sensing devices and methods for their fabrication.

BACKGROUND

Diabetes mellitus (commonly referred to as diabetes) is a group of metabolic disorders in which blood sugar levels remain elevated above normal levels over a prolonged period, typically resulting from defects in the body's ability to produce and/or use insulin. Worldwide, diabetes is a leading cause of morbidity and mortality, and represents a major health concern for most developed societies.

Monitoring of blood glucose is critical to controlling diabetes. If uncontrolled, diabetes can lead to a variety of serious life-threatening complications such as heart disease, stroke, blindness, and limb amputation. To avoid these complications, diabetics must maintain a healthy diet, exercise, take all prescribed medication, and comply with physician-established blood glucose testing schedules.

Self-monitoring of blood glucose (SMBG) has been established as a valuable tool for the management of diabetes. SMBG devices require the user to obtain a blood sample using a lancet. This blood sample is then placed onto a test strip, which is then inserted into a monitor device. This monitor device provides the user with current blood glucose level information. If blood glucose levels are outside of the normal range, then a diabetic user must take corrective action. Hyperglycemic levels require the diabetic to inject insulin, while hypoglycemic levels require the diabetic to ingest food with glucose or simple carbohydrates. The goal of SMBG is to help the patient achieve and maintain normal blood glucose concentrations in order to delay or even prevent the progression of microvascular and macrovascular complications. SMBG can also be useful for providing real-time information for adjusting medications, dietary regimens, and physical activity in order to achieve glycemic goals.

Since the work of Clark and Lyons in 1962 (Clark, L.; Lyons, C.; "Electrode Systems for Continuous Monitoring in Cardiovascular Surgery"; Ann. NY Acad. Sci. 1962, 102, 29-45), amperometric biosensors have been intensively studied. Operation of amperometric biosensors requires a conjugation between enzyme and electrochemical reactions. Amperometric biosensors monitor currents generated when electrons are exchanged either directly or indirectly between a biological system and an electrode. Generally, glucose measurements are based on interactions with one of three enzymes: hexokinase, glucose oxidase (GOx), or glucose-1-dehydrogenase (GDH)—with glucose biosensors for SMBG typically being based on the latter two enzyme families (GOx and GDH). GOx is advantageous in that it is easily obtainable, inexpensive, and able to withstand greater extremes of pH, ionic strength, and temperature relative to many other enzymes.

There are three main parts of a biosensor. The first part is a biological recognition element. In a glucose monitoring biosensor, this is the enzyme that reacts with glucose. A common enzyme used as a biological recognition element is glucose dehydrogenase flavin adenine dinucleotide (GDH-FAD). The second part of a biosensor is a transducer. The transducer converts the transfer of electrons into current output. The third part of a biosensor is a processing system that transforms the current output to a glucose output reading, thereby providing results that are easily interpretable.

Multiple types of amperometric biosensors for measuring glucose have been developed. Various general strategies for electrochemical sensing of glucose have included measuring oxygen consumption, measuring the amount of hydrogen peroxide produced by the enzyme reaction, or using a diffusible or immobilized mediator to transfer electrons from an enzyme (e.g., GOx) to an electrode.

First generation amperometric biosensors were based on direct electrochemical detection of a substrate or a product of an enzyme reaction, typically with oxygen being used as the final electron acceptor. In the case of oxidases as a subclass of enzymes, oxygen and hydrogen peroxide embody the substrate and the product, respectively. A basic operating principle of a glucose biosensor utilizing GOx is that the immobilized GOx catalyzes the oxidation of $\beta$-D-glucose by molecular oxygen producing gluconic acid and hydrogen peroxide. Hydrogen peroxide is oxidized at a catalytic (e.g., platinum) electrode. Electrodes modified with Prussian Blue (ferric hexacyanoferrate) have been substituted for platinum to serve as an electrocatalyst for hydrogen peroxide reduction, whereby hydrogen peroxide may be detected in the presence of oxygen by both electrooxidation and electroreduction at the Prussian Blue-modified electrodes. One limitation of first generation glucose biosensors is that oxygen from the surroundings can affect the glucose output levels of these devices. A high operating potential may be required to provide high selectivity.

Second generation amperometric biosensors contain soluble or immobilized electron mediators that are able to oxidize an enzyme active site. Non-physiological electron acceptors called redox mediators (also known as redox probes) are able to carry electrodes from the enzyme to the surface of a working electrode. A reduced mediator is formed instead of hydrogen peroxide, and such mediator is reoxidized at the electrode to provide an amperometric signal while regenerating the oxidized form of the mediator. Examples of electron mediators include ferrocene, ferricyanide, quinines, tetrathiafulvalene (TTF), tetracyanoquinodimethane (TCNQ), thionine, methylene blue, and methyl viologen. Potassium ferricyanide is a typical redox mediator. GDH-FAD is a common enzyme in second generation devices and does not react with oxygen but can react with sugars in the body other than glucose. Although these devices eliminate possible errors from oxygen, redox mediators are typically toxic. Additionally, second generation systems may not be well-suited for detection of low substrate (e.g., glucose) concentrations due to high noise current attributable to ferrocene primary oxidation.

Third generation amperometric biosensors are devoid of reagents and are based on direct transfer between the enzyme and the electrode without mediators (which frequently exhibit high toxicity). Rather than using mediators, an electrode can perform direct electron transfers using organic conducting materials based on charge-transfer complexes. A few enzymes such as peroxidases have been demonstrated to exhibit direct electron transfer at normal electrode surfaces. Other direct electron transfer approaches that have been studied include tetrathiafulvalene-tetracyanoquinodimethane (TTF-TCNQ), the GOx/polypyrrole system, and oxidized boron-doped diamond electrodes.

Conventional biosensors for determining glucose levels in in-patient (e.g., emergency room or hospital ward) and outpatient (office or home) settings typically rely on disposable screen-printed enzyme electrode test strips. These plastic or paper strips have electrochemical cells and contain GDH-pyrroloquinoline quinone (PQQ), GDH-nicotinamide-adenine dinucleotide (NAD), GDH-flavin adenine dinucleotide (FAD), or GOx along with a redox mediator. Typically, a test strip is first inserted into a meter, and then a small drop of capillary blood is obtained from a user's fingertip with a lancing device, and is applied to the test strip. Finally, a conversion factor is applied and the measurement results are displayed, such as in terms of plasma glucose equivalents.

Although SMBG devices are relatively easy to use, provide fast results, and allow the user to test anywhere, noncompliance remains an issue with such devices. This is because collecting the blood sample is often painful and the test strips are expensive. The average price for a single SMBG test strip is $0.98. These test strips should not be reused, so the cost can add up quickly when testing multiple times a day.

Despite the availability of various biosensors for monitoring blood glucose, it may be challenging for patients to consistently maintain an adequate supply of unexpired biosensors (e.g., test strips) on hand at all times and/or to rapidly procure replacement biosensors when needed. Biosensors are only effective if the enzymes therein are active. Once a package containing biosensors is opened, the contents are subject to exposure to humidity and chemicals in the atmosphere, which tends to hasten biosensor degradation. Replacement biosensors also entail inflated costs due in part to the necessity for such sensors to be packaged, warehoused, and distributed to users—with such distribution often including medical supply companies as intermediaries between customers and manufacturers. Aspects of the present disclosure address one or more of various limitations associated with conventional biosensors, such as their production, packaging, storage, and distribution.

SUMMARY

Aspects of the present disclosure relate to a blood glucose sensing device fabricated by three-dimensional printing, and a method for fabricating such a device. Electrodes of a blood glucose sensing device are three-dimensionally printed and comprise graphene, thereby providing enhanced electrical conduction relative to various other electrode materials. A blood glucose sensing device as disclosed herein may be embodied in a test strip configured to cooperate with a monitor device.

In one aspect, the present disclosure relates to a blood glucose sensing device comprising: a substrate; a plurality of three-dimensionally printed electrode leads comprising graphene arranged on or over the substrate; and glucose monitoring chemistry arranged in or on at least one three-dimensionally printed electrode lead of the plurality of three-dimensionally printed electrode leads.

In certain embodiments, the glucose monitoring chemistry is adsorbed in the at least one three-dimensionally printed electrode lead of the plurality of three-dimensionally printed electrode leads. In certain embodiments, the plurality of three-dimensionally printed electrode leads further comprises a thermoplastic material, such as (but not limited to) an aliphatic polyester.

In certain embodiments, the substrate comprises a polymer film, such as (but not limited to) polyester terephthalate.

In certain embodiments, the glucose monitoring chemistry comprises at least one enzyme. In certain embodiments, the at least one enzyme comprises glucose oxidase, glucose-1-dehydrogenase, or a peroxidase. Other enzymes may be used.

In certain embodiments, the glucose monitoring chemistry comprises oxygen as a final electron acceptor. In certain embodiments, the glucose monitoring chemistry comprises a redox mediator. In certain embodiments, the glucose monitoring chemistry is configured for direct electron transfer between an enzyme and at least one three-dimensionally printed electrode lead without a redox mediator.

In certain embodiments, the plurality of three-dimensionally printed electrode leads comprises a reference electrode lead, a counter electrode lead, and a working electrode lead. In certain embodiments, the counter electrode lead is longer than each of the working electrode lead and the reference electrode lead. In certain embodiments, an end portion of the counter electrode lead partially surrounds an end portion of the working electrode lead. In certain embodiments, the working electrode lead comprises a resistivity of less than $1000\Omega$.

In certain embodiments, each three-dimensionally printed electrode lead of the plurality of three-dimensionally printed electrode leads comprises a plurality of fused dots, rods, and/or layers.

In another aspect, the disclosure relates to a method for fabricating at least one blood glucose sensing device, the method comprising: three-dimensionally printing a plurality of three-dimensionally printed electrode leads comprising graphene arranged on or over a substrate; and providing glucose monitoring chemistry in or on at least one three-dimensionally printed electrode lead of the plurality of three-dimensionally printed electrode leads.

In certain embodiments, said providing of glucose monitoring chemistry in or on the at least one three-dimensionally printed electrode lead comprises soaking the at least one three-dimensionally printed electrode lead in an enzyme solution.

In certain embodiments, said providing of glucose monitoring chemistry in or on the at least one three-dimensionally printed electrode lead comprises depositing at least one enzyme concurrently with the three-dimensional printing of the at least one three-dimensionally printed electrode lead of the plurality of three-dimensionally printed electrode leads.

In certain embodiments, the at least one blood glucose sensing device comprises the substrate. In certain embodiments, the plurality of three-dimensionally electrode leads comprises a reference electrode lead, a counter electrode lead, and a working electrode lead. In certain embodiments, each three-dimensionally printed electrode lead of the plurality of three-dimensionally printed electrode leads comprises a plurality of fused dots, rods, and/or layers.

In certain embodiments, the plurality of three-dimensionally printed electrode leads comprises a plurality of reference electrode leads, a plurality of counter electrode leads, and a plurality of working electrode leads, and the method further comprises separating the substrate into a plurality of glucose sensing devices each including a reference electrode lead, a counter electrode lead, and a working electrode lead.

In another aspect, any one or more aspects or features described herein may be combined with any one or more other aspects or features for additional advantage. In certain embodiments, biomarkers other than glucose monitoring chemistries may be used to enable sensing of other constituents of fluid samples.

Other aspects and embodiments will be apparent from the detailed description and accompanying drawings.

BRIEF DESCRIPTION OF DRAWINGS

The accompanying drawings incorporated in and forming a part of this specification illustrate several aspects of the disclosure, and together with the description serve to explain the principles of the disclosure.

FIG. 1 is a top plan view illustration of a CAD model of a 3D printed glucose sensing device, including three electrodes printed over a substrate, according to an initial sensor design.

FIG. 2 is a perspective view illustration of a CAD model of the 3D printed glucose sensing device of FIG. 1.

FIG. 3 is a photograph of a 3D printed glucose sensing device according to the design of FIGS. 1 and 2.

FIG. 4 is a top plan view illustration of a CAD model of a 3D printed glucose sensing device including three electrodes, according to an updated sensor design.

FIG. 5A is a perspective view illustration of a CAD model of the 3D printed glucose sensing device of FIG. 4.

FIG. 5B is a perspective view illustration of a CAD model of multiple 3D printed glucose sensing devices according to the design of FIGS. 4 and 5A, with the glucose sensing devices overlying a substrate.

FIG. 6 is a top plan view photograph of a test printed 3D printed glucose sensing device according to the design of FIG. 4 and FIGS. 5A-5B, utilizing blue ABS filament material.

FIG. 7 is a top plan view photograph of an alpha prototype 3D printed glucose sensing device according to the design of FIG. 4 and FIGS. 5A-5B, utilizing Octave ABS filament material.

FIG. 8 is a top plan view photograph of a beta prototype 3D printed glucose sensing device according to the design of FIG. 4 and FIGS. 5A-5B, utilizing an ABS conductive black filament material.

FIG. 9A is a top plan view illustration of a 3D printed glucose sensing device according to the design of FIG. 4 and FIGS. 5A-5B, with addition of a red dashed circle encircling an electrode lead.

FIG. 9B is a side perspective schematic view of a portion of the electrode lead encircled in FIG. 9A, schematically illustrating the reaction of the glucose and glucose dehydrogenase reacting and generating electrons that are converted to a current output.

FIG. 10 is a plot of current versus glucose solution concentration for a 3D printed sensor fabricated of conductive black filament according to the beta prototype of FIG. 8.

FIG. 11 shows print settings utilized for producing a gamma prototype 3D printed glucose sensing device according to the design of FIGS. 4 and 5A-5B, utilizing a conductive graphene-containing polylactic acid-based filament material.

FIG. 12 is a top plan view photograph of a gamma prototype 3D printed glucose sensing device according to the design of FIG. 4 and FIGS. 5A-5B, utilizing a conductive graphene-containing polylactic acid-based filament material and fabricated with the print settings shown in FIG. 11.

FIG. 14 is a photograph of an experimental setup for performing cyclic voltammetry tests to determine desirable test parameters using (i) the working electrode lead of the gamma prototype 3D printed glucose sensing device according to FIG. 12 partially submerged in a redox probe solution in a beaker, (ii) an Ag/AgCO wire reference lead external to the sensing device, and (iii) a platinum wire counter lead external to the sensing device.

FIG. 15 is a screen print of a software dialog box showing amperometric i-t curve parameters used for tests performed using the gamma prototype 3D printed glucose sensing device shown in FIG. 14.

FIG. 16 is a photograph of a setup for performing amperometric i-t testing using the gamma prototype 3D printed glucose sensing device according to FIG. 12 partially submerged in a testing vial containing a glucose solution, with all three leads of the 3D printed glucose sensing device being coupled to a potentiostat machine.

FIG. 17 is a plot of current versus voltage obtained from amperometric i-t testing using the gamma prototype 3D printed glucose sensing device according to FIG. 12 and the setup described in FIG. 16, with a superimposed dashed-line circle corresponding a location (e.g., bias voltage value) providing an optimal current response.

FIG. 18 provides plots of coefficient of determination (RSQ) (left axis) and slope (right axis) versus time obtained from amperometric i-t testing using the gamma prototype 3D printed glucose sensing device according to FIG. 12.

FIG. 19 is a plot of coefficient of determination (RSQ) versus slope obtained from amperometric i-t testing using the gamma prototype 3D printed glucose sensing device according to FIG. 12.

FIG. 20 is a plot of current versus time for a first gamma prototype 3D printed glucose sensing device according to FIG. 12 for six glucose concentrations, namely, 0, 25, 50, 100, 200, and 400 mg per dl.

FIG. 21 is a plot of current versus time for a second gamma prototype 3D printed glucose sensing device according to FIG. 12 for six glucose concentrations, namely, 0, 25, 50, 100, 200, and 400 mg per dl.

FIG. 22 is a plot of current versus time for a third gamma prototype 3D printed glucose sensing device according to FIG. 12 for six glucose concentrations, namely, 0, 25, 50, 100, 200, and 400 mg per dl.

FIG. 29 a plot of current versus glucose solution concentration with soak times of 60 and 420 minutes, overlaid with a plot of current versus glucose concentration obtained from a ZENSOR® sensor, and including linear functions fitting the respective plots.

FIG. 30 is a plot of current versus glucose solution concentration embodying a calibration curve for multiple 3D printed glucose sensing devices based on current readings at 3 seconds, with a linear function fitting the plotted data points.

FIG. 31 is a plot of current versus glucose solution concentration embodying a calibration curve for multiple 3D printed glucose sensing devices based on current readings at 13 seconds, with a linear function fitting the plotted data points.

FIG. 32 is a plot of current versus glucose solution concentration embodying a calibration curve for multiple 3D printed glucose sensing devices based on current readings at 42.3 seconds, with a linear function fitting the plotted data points.

FIG. 33 is a normal probability plot of residual versus glucose concentration for multiple 3D printed glucose sensing devices at a time of 3 seconds.

FIG. 34 is a normal probability plot of residual versus glucose concentration for multiple 3D printed glucose sensing devices at a time of 13 seconds.

FIG. 35 is a normal probability plot of residual versus glucose concentration for multiple 3D printed glucose sensing devices at a time of 42.3 seconds.

FIG. 38 is a normal probability plot of standardized residual versus predicted current value for glucose concentrations at time of 42.3 seconds obtained with a 3D printed strip sensor.

FIG. 39 is a table identifying costs of materials used in a 3D printed strip sensor.

DETAILED DESCRIPTION

Figure 13:
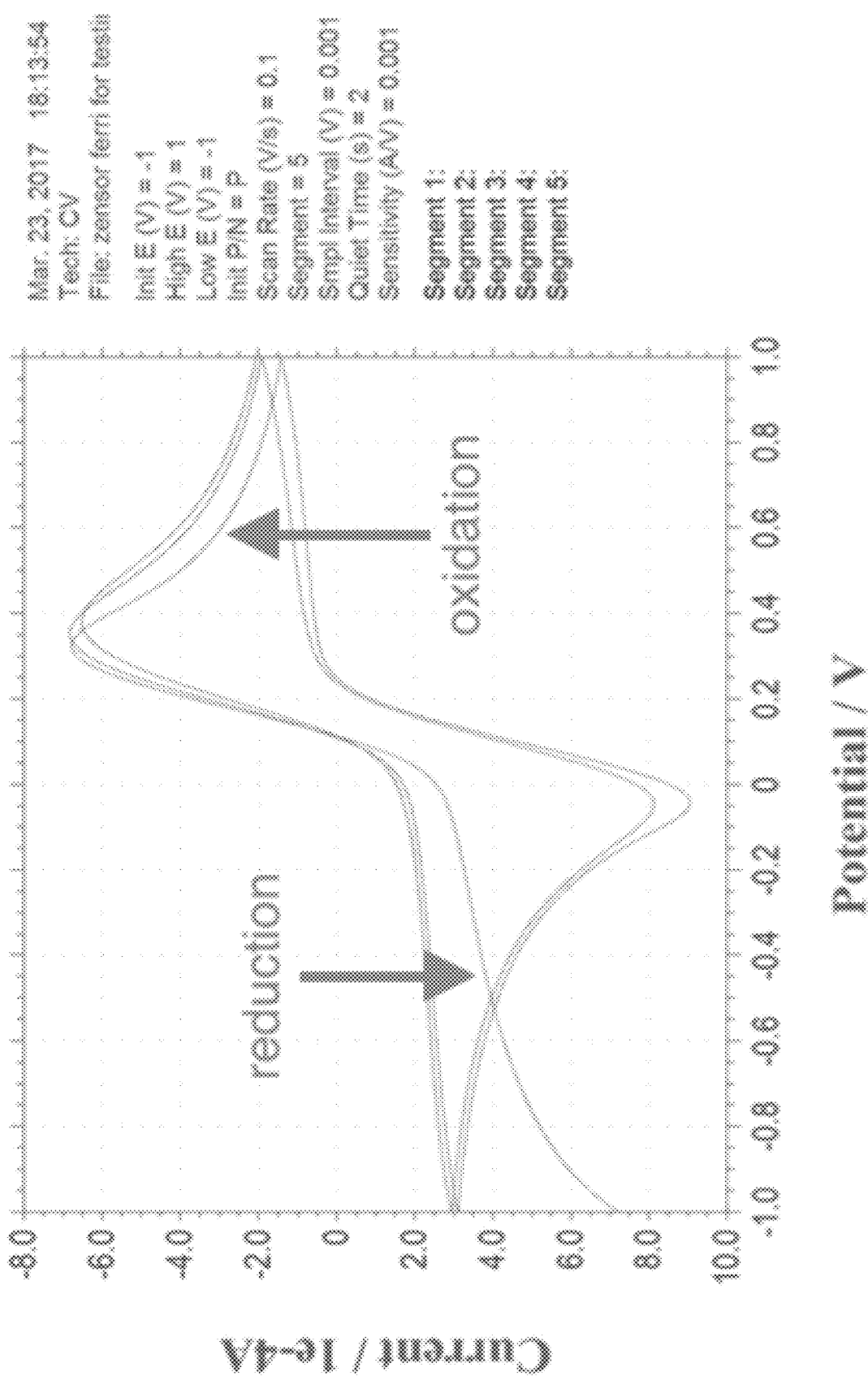
FIG. 13 is a plot of current versus potential generated by cyclic voltammetry testing of a ZENSOR® sensor utilizing a redox probe solution and a CHI 1230A potentiostat machine.

As noted previously, aspects of the present disclosure relate to a blood glucose sensing device fabricated by three-dimensional printing, and a method for fabricating such a device. Sensing devices suitable for use with other enzymes and/or biomarkers are also contemplated within the scope of the present disclosure.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

3D manufacturing is a developing technology that could change how diseases, such as diabetes, are monitored and managed. As availability and functionality of 3D printers expand, this technology will potentially create a new detection method as an alternative to the current market standard of self-monitoring-blood-glucose (SMBG) devices. This disclosure presents an example of a proof-of-concept 3D printed glucose sensor with similar features to current lab-industry standards. The sensor was verified to detect physiological glucose concentrations between 0-400 mg/dL with a linear coefficient as high as 0.9665. 3D-printed test strips are a novel technology that would provide individuals with diabetes with a cost-effective method of managing their disease. Additionally, this technology could allow detection of different biomarkers and thereby further enhance disease management.

3D-Printing Overview

Additive manufacturing is the technique of building objects by layering material. 3D printing is one of the most popular forms of additive manufacturing. In 3D printing, a computer aided design (CAD) file of the object is created on a software program. One example of a common software program suitable for use with various 3D printing systems is SOLIDWORKS® (Dassault Systems SolidWorks Corporation, Waltham, Mass., USA). The CAD file is then transferred to the 3D printer software for printing to begin. The designed object is created by adding layers of material on top of each other. Materials that may be used in 3D printing include various types of plastics, metals, waxes, carbons, and even biomaterials.

3D printing results in formation of multiple fused elements, typically including a plurality of rods, dots, and/or layers of one or more materials. These various rods, dots, and/or layers may be deposited over a substrate and fused by addition of energy (e.g., impingement of laser emissions) and cooling. 3D printed materials may be used to form various two- and three-dimensional shapes.

Although 3D printing was developed in the early 1980s, it has recently grown in popularity and use due to the development of low-cost 3D printers. Newer user-friendly software has allowed the development of unique uses for 3D printers. This ultimately has transformed 3D printing from an expensive method to develop trinkets, to an inexpensive means to develop industrial goods. 3D printing also has many distinct benefits when compared to traditional manufacturing, including easier customization of objects, shorter time required to build an object from a design, and simplification of the manufacturing process. This proves beneficial not only to the process of prototyping, but also to companies trying to get products on the market quickly. It also reduces wasted materials, which is part of the reason that it is much more cost effective than traditional manufacturing in certain contexts.

Development of CAD Model for Initial Sensor Design with 3D Printed Substrate and Electrodes A 3D printed glucose sensing device according to an initial design incorporating a 3D printed substrate as well as 3D printed electrode leads was designed using SOLIDWORKS® computer aided design (CAD) software. A three-lead design was selected because it embodies an industry standard and allows for counter, working, and reference electrode leads. The final SOLIDWORKS® CAD model of the 3D printed sensor according to the initial design is shown in FIGS. 1 and 2. The model of the sensing device 5 includes a working lead 10, as well as a reference lead 20 and a counter lead 30 that laterally displaced to either side of the working lead 10. The counter lead 30 is longer than the reference lead 20, which is longer than the working lead 10. The working lead 10, the reference lead 20, and the counter lead 30 each include a connection end 12, 22, 32 and a sensing end 14, 24, 34 arranged between an intermediate segment 16, 26, 36 respectively. Each connection end 12, 22, 32 has an increased width relative to each intermediate segment 16, 26, 36. The sensing ends 24, 24 of the reference lead 20 and the counter lead 30 are curved in a medial direction to terminate at an imaginary line (not shown) extending through the working lead 10, while the sensing end 14 of the working lead 10 is straight (i.e., collinear with the intermediate segment 16). The working lead 10, the reference lead 20, and the counter lead 30 are arranged on a printed substrate 40. In one embodiment, the counter lead 30 may include a length of about 32.67 mm, an aggregate width extending between outer corners of connection ends 12, 32 of the reference lead 20 and the counter lead 30 may be about 10.75 mm, and the substrate 40 may include a thickness of about 0.40 mm.

A photograph of 3D printed glucose sensing device 5A, produced according to the initial design of FIGS. 1 and 2, is shown in FIG. 3. The sensing device 5A according to the initial design did not prove acceptable for multiple reasons. Firstly, it required two extruders for printing, which resulted in many sensing devices being wasted due to calibration issues. In addition, all amperometric i-t tests performed on sensing devices according to the initial design were highly variable and produced very low current outputs. Challenges with printing and/or testing 3D printed glucose sensing devices according to the initial design of FIGS. 1 and 2 led to the creation of updated designs.

Development of the CAD Model of Updated Sensor Design with 3D Printed Electrode Leads over Preformed Substrate An updated SOLIDWORKS® model of a sensing device 55, shown in FIGS. 4 and 5A, was created to more closely resemble the structure, dimensions, and design of an industry standard sensor, the ZENSOR® TE100 SPE sensor (Zensor R&D Company, Taichung City, Taiwan). Both the 3D printed sensing device 50 and ZENSOR® sensors had an electrode with a three-lead design with a 3 mm working diameter. The design of the printed sensing device 50 allowed data output from the 3D printed sensor to be more easily compared to that of the ZENSOR® sensor. The 3D printed sensor according to the updated design did not include a printed substrate; instead, electrodes were printed onto a prefabricated Mylar® polyester terephthalate (DuPont Teijin Films, Chester, Va., US) substrate that was secured to the printing platform of the printer.

Referring to FIGS. 4 and 5A, the sensing device 55 includes a working lead 60, as well as a reference lead 70 and a counter lead 80 that laterally displaced to either side of the working lead 60. The counter lead 80 is longer than the working lead 60, which is longer than the reference lead 70. The working lead 60, the reference lead 70, and the counter lead 80 each include a connection end 62, 72, 82 and a sensing end 64, 74, 84 arranged between an intermediate segment 66, 76, 86 respectively. Each connection end 62, 72, 82 has an increased width relative to each intermediate segment 66, 76, 86. The sensing end 64 of the working lead 60 has circular shape of increased width relative to the intermediate segment 66. The circular-shaped sensing end 64 may embody a 3 mm working diameter. The sensing end 74 of the reference lead 70 is angled in a medial direction toward the (circular shaped) sensing end 64 of the working lead 60. The sensing end 84 of the counter lead 80 comprises a semi-annular shape that curves around a portion of the sensing end 64 of the working lead 60, with an angled segment 83 extending between the sensing end 84 and the intermediate segment 86 of the counter lead 80. The angled segment 83 of the counter lead 80 resembles a mirror image of the (angled) sensing end 74 of the reference lead 70. The modeled sensing device 55 includes the working lead 60, reference lead 70, and counter lead 80 in the absence of a printed substrate, although it is to be recognized that such leads 60, 70, 80 may be printed over any suitable preformed substrate. In one embodiment, the working lead 60, reference lead 70, and counter lead 80 may include a height (or thickness) of about 0.95 mm, with the counter lead 80 including a total length of about 37.72 mm, and an aggregate width extending between outer corners of connection ends 72, 82 of the reference lead 70 and the counter lead 80 may be about 11.07 mm.

FIG. 5B shows multiple (i.e., nine) sensing devices 55 according to the design of FIGS. 4 and 5A on a MAKERBOT® printer build plate 56 (MakerBot Industries, LLC, Brooklyn, N.Y., USA). It is contemplated that multiple sensors may be printed on a single substrate, and then separated from one another by any suitable means (e.g., cutting, etching, locally weakening, or scoring the substrate between different sensor areas).

Test 3D Print of CAD Model According to Updated Sensor Design

With the updated CAD model, test prints of sensing devices 55 according to the design of FIGS. 4 and 5A were conducted to see if the printer resolution was sufficiently fine for the details of the sensor and if the sensor could be printed onto the Mylar substrate. For an initial test print, a blue ABS filament (Adafruit, USA) was used in a MAKERGEAR® Printer (MakerGear, LLC, Beachwood, OH, USA). This filament was chosen because it is a common printing filament that is readily available. As shown in FIG. 6, the 3D printer successfully printed a test sensor 55T including multiple electrodes (i.e., a working lead 60T, a reference lead 70T and a counter lead 80T) onto a substrate 58 with high resolution. However, the electrodes of the printed test sensor 55T were not conductive, such that the test sensor 55T did not provide the desired utility. The resistance of the working lead 60T, which includes a circular sensing end 64T, was determined to be hundreds of mega ohms for three centimeters of filament, meaning that the filament was nonconductive. Filament material with such a high electrical resistance would not allow electrons to move freely through the sensor, so it was determined that a more conductive filament would be necessary Development of Alpha Prototype of 3D-Printed Sensor According to Updated Sensor Design The Octave ABS filament (Octave Systems, Inc., USA) was determined to be more conductive with a preprinted resistance of about 37 MOhm for three centimeters. The updated CAD file (embodying the same model represented in FIGS. 4 and 5A) was printed using the MAKERGEAR® printer. An alpha prototype printed sensor 55A, including multiple electrodes (i.e., a working lead 60A, a reference lead 70A, and a counter lead 80A) formed over a substrate 58A is shown in FIG. 7. The print quality was still reasonably good and provided a printed resistance of around 30 M Ohms for the length of the working lead 60A, which terminated at a circular sensing end 64A. Although this resistance was lower than the previously 3D printed sensors, the resistance was still too high for an electrochemical sensor. The resistance of the working lead of a ZENSOR® sensor is about 100 Ohms, so it was determined that a 3D-printed electrode should utilize a filament providing comparable or similar properties.

Development of Beta Prototype of 3D-Printed Sensor According to Updated Sensor Design To increase the electrochemical properties of a 3D printed sensor according to the design of FIGS. 4 and 5A, an ABS conductive black filament (Black Magic 3D, USA) was purchased. This filament was advertised to be conductive with a preprinted resistance on the order of kilo ohms; however, it was determined that the preprinted resistance was approximately 20 M Ohms per three centimeters. The difference in resistivity could be due to manufacturing impurities or errors (it is noted that this filament is no longer sold by the manufacturer). The updated CAD model of FIGS. 4 and 5A was printed using this filament to form multiple electrodes (i.e., a working lead 60B, a reference lead 70B and a counter lead 80B, with the working lead 60B terminating at a circular sensing end 64B) over a Mylar substrate 58B using the MAKERGEAR® printer to form a beta prototype printed sensor 55B as shown in FIG. 8. Although optimal printer settings had to be determined again, printing the ABS conductive black filament with carbon still proved to be challenging. The retraction settings of the 3D printer were increased to the maximum level to reduce the bleeding of the electrode leads. The extruder head temperature was increased to 220° C. (which was critical for the filament not to clog the extruder head) and the platform temperature was increased to 55° C. These changes prevented the printer from etching electrodes of the sensor 55B into the Mylar substrate 58B without extruding out filament. The resolution of the 3D-printed sensor with this filament was not ideal, so after each print, a razor (not shown) was used to separate areas of the leads 60B, 70B, 80B that had bled together.

FIG. 9A is a top view illustration of electrodes (including a working lead 60, a reference lead 70, and a counter lead 80) of a 3D printed sensor according to the design of FIGS. 4 and 5A, with addition of a dashed circle 88 encircling the circular shaped sensing end 64 of the working lead 60. FIG. 9B is a side perspective schematic view of the circular shaped sensing end 64 encircled in FIG. 9A, with glucose monitoring chemistry 65 arranged on the sensing end 64, and schematically illustrating the reaction of glucose and glucose dehydrogenase to generate electrons ($e^-$) that are converted to a current output.

The printed resistance of the working lead of the electrode of the beta prototype sensor 55B of FIG. 8 was determined to be approximately 22 MOhm. Due to a somewhat smaller resistance compared to the previous 3D printed sensors, the electrochemical properties of this sensor 55B were tested. The current output at various glucose concentrations was measured for the 3D printed sensor 55B and compared to the ZENSOR® sensor. Multiple examples of the 3D printed sensor 55B produced current output values that were two to three orders of magnitude less than the ZENSOR® current output values. This demonstrated that the resistance was still too high for the electrical sensor. The R-squared value for this data was determined to be very low at 0.01, as seen in FIG. 10. The inconsistencies of the physical characteristics of the 3D printed sensors 55B were determined to be the cause for the extremely low R-squared value. The inconsistencies included differences in porosity, mass, and density of the filament between the 3D printed sensors 55B. Data (current versus glucose solution concentration) obtained from the beta prototype of the 3D printed sensor 55B including conductive black filament material is plotted in FIG. 10. Such figure shows that a more conductive filament and a printer with a higher resolution would be desirable.

Development of Gamma Prototype of 3D-Printed Sensor According to Updated Sensor Design A conductive graphene-containing filament was ordered (Black Magic 3D, USA), with a preprint resistivity of 1.8 W per three centimeters. Graphene was determined to be a good material as it is strong, flexible, and conductive. This filament is a polylactic acid (PLA) based filament, so a MAKERBOT® printer specifically designed for PLA filaments was used to increase the resolution and quality of the print. To adjust the print settings, the custom settings button was selected. The temperature settings for the extruder were changed to 220° C., as this was determined to be the melting point for the conductive graphene filament. The infill density was selected to be 100% to create a solid print and maximize the conductivity of the sensor. The travel speed was changed to 30 mm/s, as this was determined to produce a print with the highest resolution and prevent slipping. The retraction distance was also adjusted from 0.5 mm to 1.5 mm. This change was important to prevent the filament from oozing out of the extruder between layers. The final printer settings are shown in FIG. 11, to produce 3D printed sensors according to the design of FIGS. 4A and 5.

In preparation for 3D printing, a Mylar substrate was taped onto the platform of the printer, and the filament was loaded into the printer. Taping the Mylar substrate was determined to be beneficial to ensure that no warping occurred during the print.

The graphene-containing filament proved to be challenging to use, since even after desirable print settings were determined, the resulting sensors still embodied some inconsistencies that could be visually observed. To mitigate these inconsistencies, a razor was used to thoroughly and precisely clean filament that had bled between the three leads. After gamma prototype sensors were printed, the working lead of the electrode was determined to have a resistivity of approximately 700 W. This was much more comparable to the ZENSOR® sensor resistivity of approximately 100 W. A photograph of a gamma prototype sensor 55G produced by 3D printed with the conductive graphene filament is shown in FIG. 12. The gamma prototype 3D printed sensor 55G, including multiple electrodes (i.e., a working lead 60G, a reference lead 70G, and a counter lead 80G, with the working lead 60B terminating at a circular sensing end 64G) formed over a substrate 58G. Multiple examples of the gamma prototype 3D printed sensor were produced.

Before testing could be conducted on the gamma prototype conductive graphene 3D-printed sensors, specific testing parameters had to be determined. Electrochemical analyzer CV (current versus voltage) testing was performed on a ZENSOR® sensor with various concentrations of redox probe at various voltages to determine the suitable parameters for amperometric i-t testing.

Chemicals and Reagents

All the chemicals used in experiments described herein were purchased through Sigma-Aldrich unless stated otherwise. The enzyme used in these experiments, glucose dehydrogenase flavin adenine dinucleotide (GDH-FAD), was donated from Amano Inc. (Japan). The GDH-FAD used had an activity of 209 U/mg. Phosphate-buffered saline (PBS), with a pH of 7.4, was used to prepare all glucose solutions, the redox probe solution, and the enzyme solution.

Making Redox Probe Solution

To test the electrochemical properties of the sensor, a reagent mixture was created. This mixture consisted of enzyme and a redox probe. To create the redox probe, potassium ferricyanide and phosphate buffered saline (PBS) were mixed together to form a solution with a concentration of 100 mM. The mixture was stored in an amber vial because the mixture is light sensitive. This redox probe solution was mixed using a vortexer for 30 seconds and then allowed to sit for ten minutes. After ten minutes, the redox probe mixture was tested to ensure that it was made correctly. To test the redox probe, a CHI 1230A potentiostat machine (CH Instruments, Austin, Tex.) was checked to ensure that the hardware was working correctly.

A ZENSOR® sensor was then hooked up to the potentiostat using alligator clips. A red alligator clip was attached to the counter lead of the electrode. A green alligator clip was attached to the working lead of the electrode. The reference lead was then attached to a white alligator clip. The technique on the potentiostat was selected to be cyclic voltammetry. The parameters were set to have a voltage between −1V and 1V, a positive initial scan polarity, a scan rate of 0.1 V/s, 5 sweep segments, a sample interval of 0.001 V, a quiet time of 2 seconds, and a sensitivity of 1E-003 A/V. Once the parameters were set 90 µL of the redox probe mixture was pipetted onto the working circle of the ZENSOR® sensor and the run button was selected. Once the potentiostat was done running, a current verse potential graph was produced. A successful redox probe mixture could be confirmed if the graph resembled the shape and magnitude depicted in FIG. 13.

Making Enzyme Solution

To create the enzyme solution, GHD-FAD and the redox probe solution were mixed together in a one-to-one ratio, 1 mg of the GHD-FAD enzyme was mixed with 1 mL of the redox probe solution. This solution was created and stored in an amber vial, as it is light sensitive. It was lightly mixed, but not mixed on the vortexer. This is because the enzyme could be denatured by vortexing. Before using the enzyme solution, it was required to sit for ten minutes.

Making Glucose Solutions

Glucose solutions of various concentrations (0, 25, 50, 100, 200, 400 mg/dL) were prepared using PBS. A vortexer was used to mix the glucose and PBS. The solutions were prepared 24 hours prior to their use. This allowed the glucose to fully dissolve.

Determining Optimal Settings to Test 3D Printed Sensor

To determine the proper parameters for testing, cyclic voltammetry tests were conducted with control leads, with the experimental setup being shown in FIG. 14. A group of gamma prototype 3D printed sensors 55G were placed in a beaker 90 containing redox probe solution 95. Each gamma prototype 3D printed sensor 55G included multiple electrodes (i.e., a working lead 60G, a reference lead 70G, and a counter lead 80G). For purposes of the experiment, reference lead 70G of one 3D printed sensor was replaced by an Ag/AgCO wire electrode 71. The working electrode lead 60G on the 3D printed sensor 55G remained in use. The counter electrode lead 80G was replaced by a platinum wire electrode 81. The working electrode lead 60G as well as the two wire electrodes 71, 81 were placed into the beaker 90 and connected via alligator clips 91, 92, 93, respectively, to the potentiostat machine. Redox probe solutions 95 at various concentrations were added to the beaker 90 and data was collected. The voltage range was also changed to determine the optimal voltages.

Testing 3D Printed Sensor

Numerous gamma prototype 3D printed sensors produced on a single substrate (e.g., from an assembly such as shown in FIG. 5B) were separated and cut apart. The 3D printed sensors were cut so that minimal Mylar substrate material was surrounding the leads (i.e., working lead, reference lead, and counter lead). FIG. 16 shows a gamma prototype 3D printed sensor 55G with one end placed into a rectangular testing vial 100. The working lead 60G, reference lead 70G, and counter lead 80G were attached to the potentiostat machine, so that a red alligator clip 103 was attached to the counter lead 80G, a green alligator clip 101 was attached to the counter lead 60G, and the a white alligator clip 102 was attached to the reference lead 70G. The technique was selected to be amperometric i-t. The parameters were selected to that the initial voltage was 0.35V. The run time was selected to be 90 seconds for all the tests to ensure that enough data was collected to capture all trends. The remaining test parameters are shown in FIG. 15.

With continued reference to FIG. 16, once the potentiostat machine was set up, 810 µL of enzyme solution was pipetted to into the testing vial 100. Then, 90 µL of the glucose solution was pipetted into the vial 100. This liquid mixture 105 was stirred 10 times counterclockwise. One end of the gamma prototype 3D printed sensor 55G attached to the potentiostat machine was immersed into a testing vial 100 and the test was immediately started. A current verses time graph was produced, and the data was then analyzed using Microsoft Excel®.

Calibration of Gamma Prototype of 3D-Printed Electrode

Parameters for amperometric i-t testing determined according to the above-described procedures were selected to have the best signal-to-noise ratio (SNR). FIG. 17 provides a representation of the highest slope and coefficient of determination ($R^2$, also termed "RSQ") at the most optimal voltage. As shown in FIG. 17, a bias potential of 0.35V was selected, corresponding to the optimal current response observed in amperometric i-t testing. Using this voltage, the various glucose solutions were tested using amperometric i-t. An analysis determined that the electrical current at 42.3 seconds was the best representation of the signal produced by the sample, as shown in FIG. 18. At this time, the electrical current output had the highest correlation and slope. Current values at 42.3 seconds were used in the construction of calibration curves. FIG. 19 provides a peak representation of $R^2$ (also termed "RSQ" herein) versus slope.

Initial Verification of Gamma Prototype of 3D-Printed Sensor

Utilizing a 3D printed sensor having electrode leads printed with a conductive graphene filament, with a resistivity comparable to the ZENSOR® and with ideal testing parameters, an amperometric i-t test was performed. The current output was measured for glucose solutions of various concentrations. The results from this test showed that there was a positive relationship between the measured current output and the glucose concentration; however, the current differences between the various glucose concentrations were very low. This can be seen in FIGS. 20 to 22, which provide plots of current versus time for first, second, and third sensors, respectively. FIGS. 20 and 21 show the expected trend for various glucose solution concentrations, whereas FIG. 22 shows somewhat of the expected trend for various glucose solution concentrations, but with a trend not as consistent as the other sensors.

Figure 23:
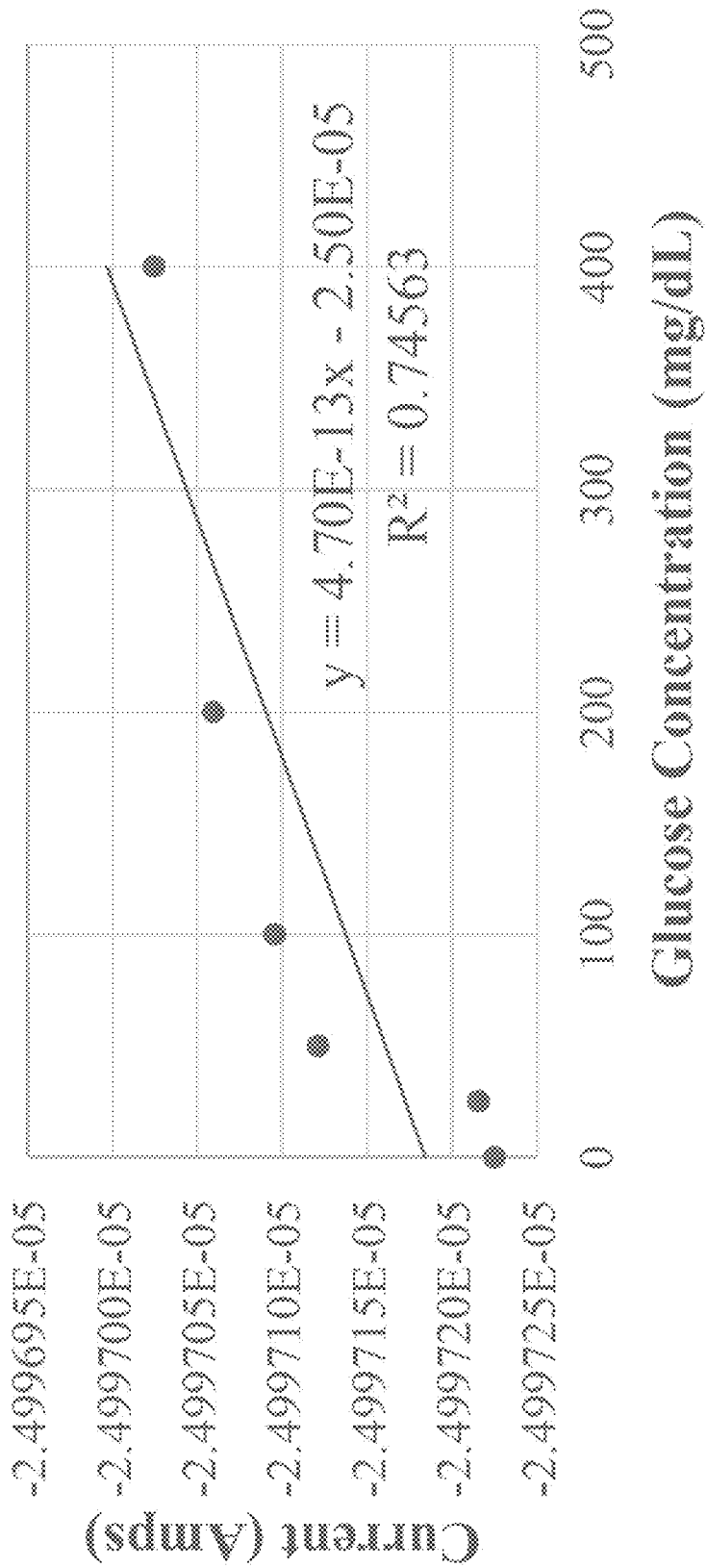
FIG. 23 is a plot of current versus glucose concentration for the first gamma prototype 3D printed glucose sensing device described in connection with FIG. 20.
Figure 24:
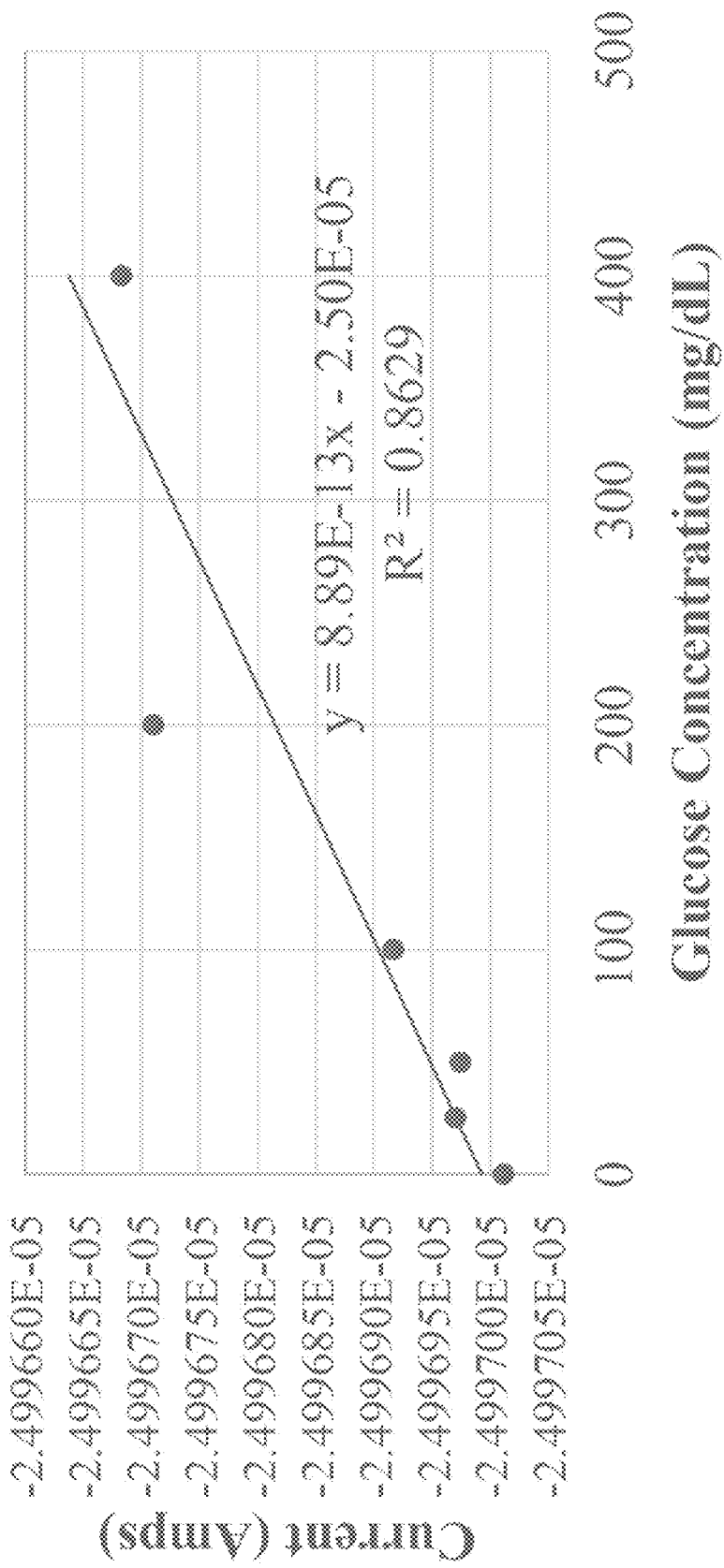
FIG. 24 is a plot of current versus glucose concentration for the first gamma prototype 3D printed glucose sensing device described in connection with FIG. 21.
Figure 25:
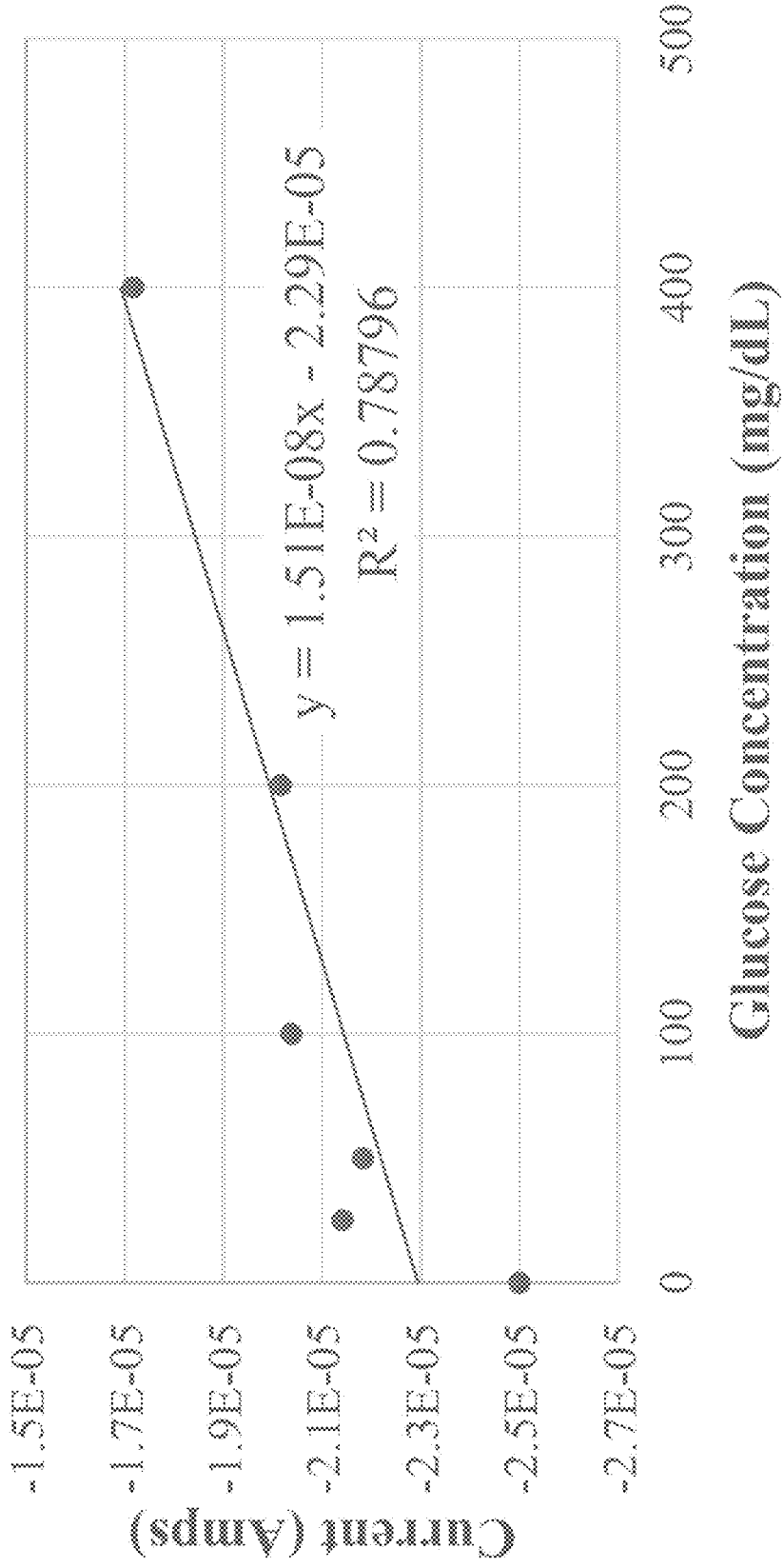
FIG. 25 is a plot of current versus glucose concentration for the first gamma prototype 3D printed glucose sensing device described in connection with FIG. 22.
Figure 26:
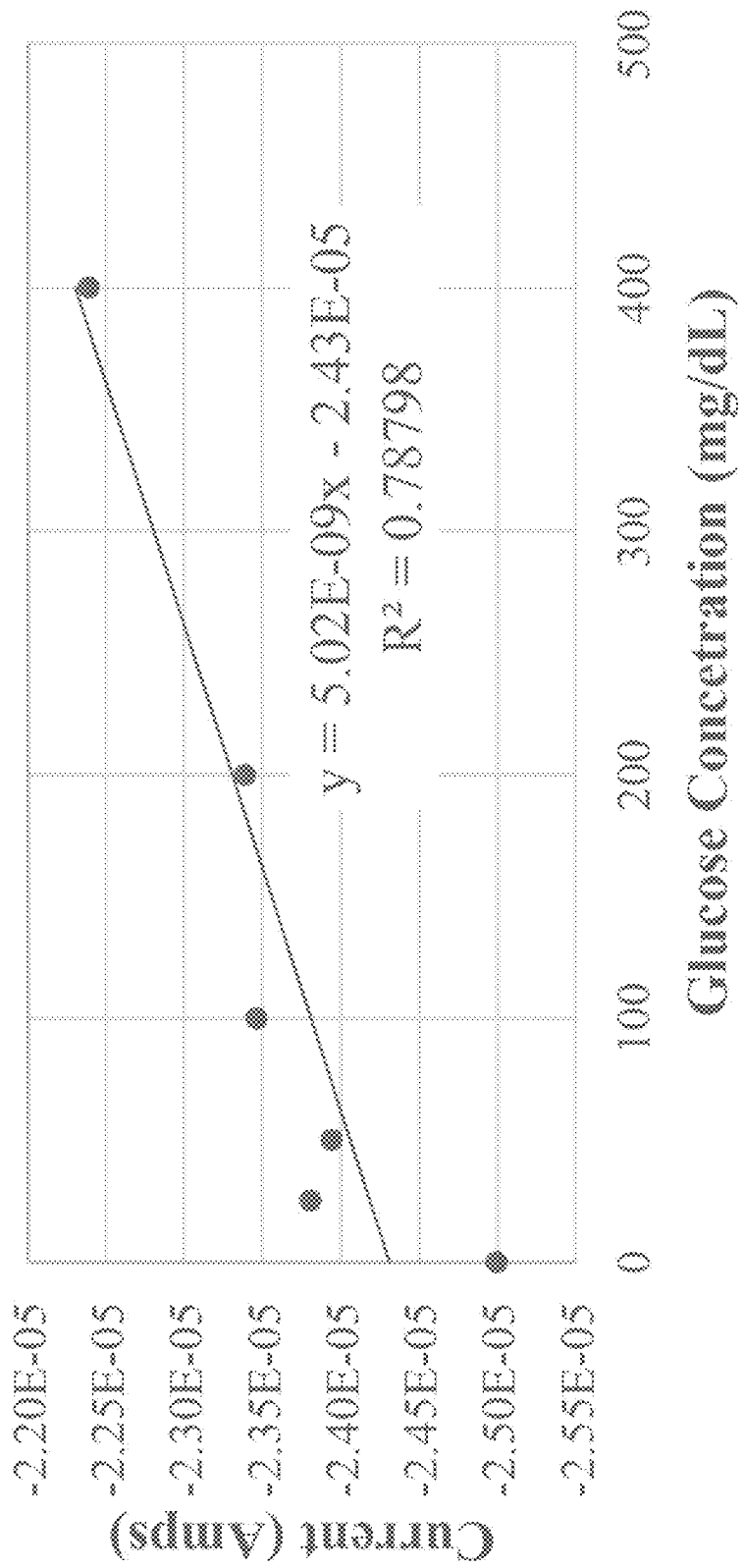
FIG. 26 is a plot over average current versus glucose concentration for the first through third gamma prototype 3D printed glucose sensing devices described in connection with FIGS. 20-25.

The foregoing data was further analyzed for the current output at 42.3 seconds. The results can be seen in FIGS. 23 to 26. FIGS. 23-25 plot current versus glucose concentration for sensors 1 to 3, respectively, and FIG. 26 provides average current versus glucose concentration for the three sensors in combination. As shown in FIG. 23, sensor 1 was determined to have an R-squared correlation value of 0.74563 and a slope of 4.70E-13x (with x representing the concentration of glucose) and the y-intercept being −2.50E-05 Amps. As shown in FIG. 24, sensor 2 was determined to have an R-squared correlation value of 0.8629 and a slope of 8.89E-13x (with x representing the concentration of glucose) and the y-intercept being −2.50E-05 Amps. As shown in FIG. 25, sensor 3 was determined to have an R-squared correlation value of 0.78796 and a slope of 1.51E-08x (with x representing the concentration of glucose) and the y-intercept being −2.29E-05 Amps. As shown in FIG. 26, the average of sensors 1, 2, and 3 was determined to have an R-squared correlation value of 0.78798 and a slope of 5.02E-09x (with x representing the concentration of glucose) and the y-intercept being −2.43E-05 Amps. This confirmed that the 3D printed graphene sensors were accurately detecting the various glucose solutions.

Post Print Modification of 3D-Printed Sensor

Figure 27:
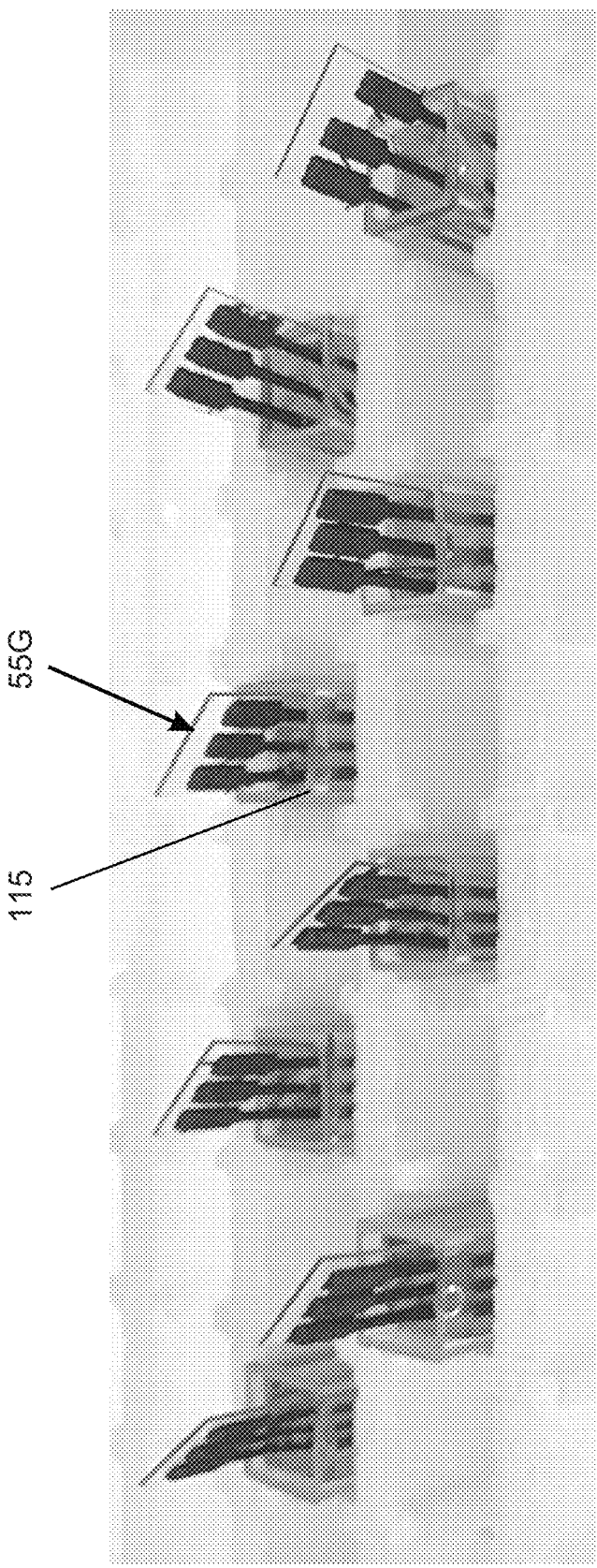
FIG. 27 is a photograph of multiple 3D printed glucose sensing devices soaking in enzyme solution containing potassium ferrocyanide to compensate for differences in density and porosity of filament material used in 3D printing electrodes of the sensing devices.

It was hypothesized that a low signal difference between glucose concentrations was due to the fact that the redox probe mixture was not reacting properly with the graphene filament due to inconsistency of the print quality. Although the printed sensors appeared to be similar, there were differences in the density and porosity of the filament. To correct for this, numerous gamma prototype 3D printed sensors 55G were placed into small vessels 115 and soaked in enzyme solution containing potassium ferricyanide for 420 minutes while in the refrigerator, as shown in FIG. 27. The procedure required using 100 mM concentration of potassium ferricyanide and 209 units/mg concentration of enzyme.

Figure 28:
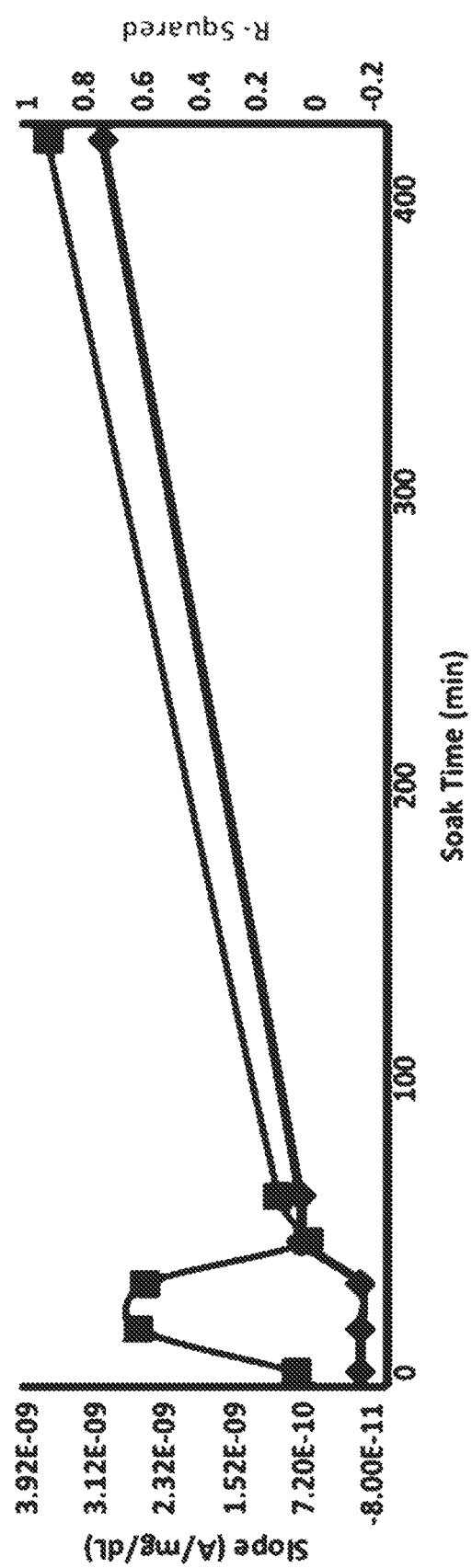
FIG. 28 is a plot of slope versus soak time, showing the effects of soak times (0, 15, 30, 45, 60, and 420 minutes) on the slope and linear correlation values.

To determine how long the 3D-printed sensors 55G needed to soak in the enzyme solution, the sensors 55G were soaked for various lengths of time. The times that were tested included: 0 minutes, 15 minutes, 30 minutes, 45 minutes, 60 minutes, and 420 minutes. Before testing, the sensors 55G were rinsed and brought up to room temperature before being placed into a testing vial. In the testing vial, 810 μL of the enzyme was thoroughly mixed with 90 μL of a glucose solution. While the sensors 55G were soaking in the enzyme solution, they were stored at 277.15K due to the temperature sensitivity of the GDH-FAD enzyme. The results from this can be seen in FIGS. 28 and 29. FIG. 28 plots slope versus soak time, showing the effects of soak times (0, 15, 30, 45, 60, and 420 minutes) on the slope and linear correlation values. FIG. 29 provides an overlay plot of current versus glucose concentration with soak times of 60 and 420 minutes. The current output for glucose solutions of various concentrations for each individual soak time were overlaid with data obtained from a ZENSOR® sensor to show that 420 minutes gave the best comparable result when compared with the ZENSOR® sensor. Soak time below 60 minutes produced a flat line when graphed alongside the scale. Additionally, the magnitude of slope increased with increasing soak time. A soak time of 60 minutes was determined not to be enough time, as the $R^2$ value was determined only to be 0.10991. Of the soak times tested, 420 minutes produced the best results, as the $R^2$ value was determined to be 0.91631. The $R^2$ value for the 420-minute soak time was comparable to the $R^2$ value of the ZENSOR® sensor, which was determined to be 0.98635. Soaking the electrodes allowed for the enzyme solution to fill in the pores of the printed sensor, which allowed for easier movement of electrons through the working sensor, resulting in an increase in the current output.

Quality Control of 3D-Printed Sensor

The electrodes were printed and prepared in batches of nine. Each electrode was analyzed using Ampi-t at 0.35 volts. The baseline current output readings were compared and the sensors were placed into batches containing sensors that produced similar baseline current output readings. Placing sensors into batches according to baseline readings is a standard procedure in the SMBG device industry.

Verification of Soaked Gamma Prototype of 3D-Printed Sensor

The current output for the soaked 3D-printed sensors were compared and calibration curves were created. Although 42.3 seconds was determined to be the optimal current output time, calibration curves were also created for 3 seconds and 13 seconds. These times were selected to generate a more reasonable range for SMBG devices when compared to the optimal experimental current output time. FIG. 30 is a representation of the 3D printed strip sensor calibration curve with glucose solutions based off current readings at 3 seconds (N=4). FIG. 31 is a representation of the 3D printed strip sensor calibration curve with glucose solutions based off current readings at 13 seconds (N=4). FIG. 32 is a representation of the 3D printed strip sensor calibration curve with glucose solutions based off current readings at the optimal time of 42.3 seconds (N=4). Error bars shown for all figures are standard error. FIG. 33 is a normal probability plot of residual versus glucose concentration at 3 seconds. FIG. 34 is a normal probability plot of residual versus glucose concentration at 13 seconds. FIG. 35 is a normal probability plot of residual versus glucose concentration at 42.3 seconds. After 13 seconds in the residual plots, there is no obvious pattern when plotting the residual versus the run order, which is evident of a good model.

As seen in FIG. 32, the calibration curve for 42.3 seconds was determined to have an R-squared correlation value of 0.9665, a slope of −3.14E-09x (with x representing the concentration of the glucose solution), and a y-intercept of −3.45E-07 Amps. As seen in FIG. 31, the calibration curve for 13 seconds was determined to have an R-squared correlation value of 0.93614, a slope of −3.20E-09x (with x representing the concentration of the glucose solution), and a y-intercept of −4.16E-07 Amps. As seen in FIG. 30, the calibration curve for 3 seconds was determined to have an R-squared correlation value of 0.798, a slope of −3.50E-09x (with x representing the concentration of the glucose solution), and a y-intercept of −6.44E-07 Amps.

The calibration curve at 13 seconds is significantly better than the calibration curve at 3 seconds. Although the calibration curve at 42.3 seconds is slightly better than the calibration curve at 13 seconds, the improvements are negligible. This means that the current outputs at and after 13 seconds are just as reliable as the current outputs at the optimal time of 42.3 seconds.

To determine if the calibration curves fit the data well, the residuals were plotted for the three current output times. As shown in FIG. 33, it was determined that the calibration curve at 3 seconds did not fit the data well, as the residuals were not random and a pattern could be observed. As shown in FIG. 34, it was determined that the calibration curve at 13 seconds did fit the data well, as the residuals were random and had a relatively constant spread, allowing a linear regression model to be used. The calibration curve at 42.3 seconds was also determined to be a good fit to the data, as seen in FIG. 35. FIG. 35 shows that the residuals do not have a visible pattern and were not spread unevenly. This also supported that a linear regression model fit the data.

Figure 36:
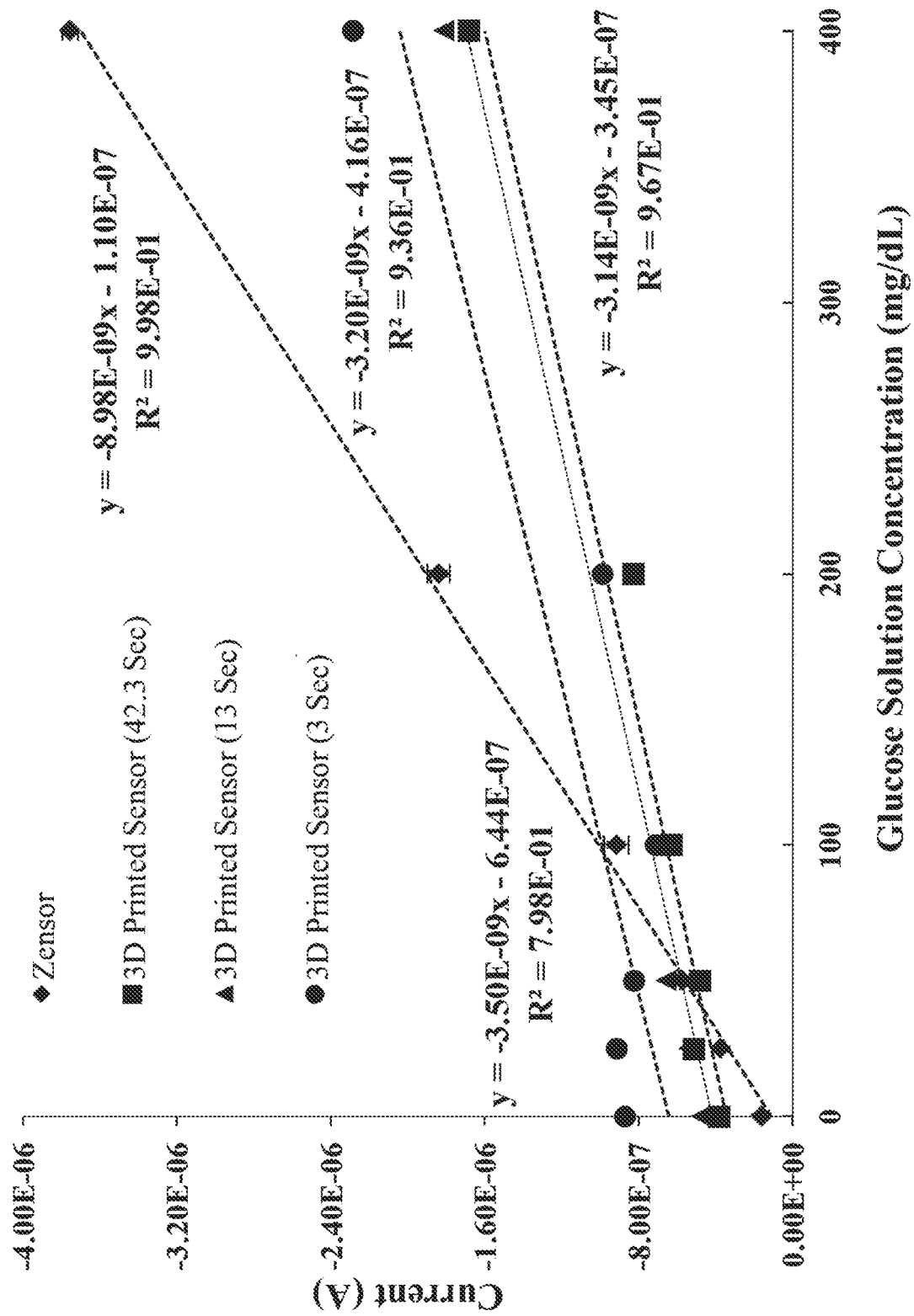
FIG. 36 provides plots of current versus glucose concentration for a 3D-printed sensor based on readings at 3 seconds, 13 seconds, and 42.3 seconds, as well as for a ZENSOR® sensor, together with linear function fittings for the four series of plotted data points.
Figure 37:
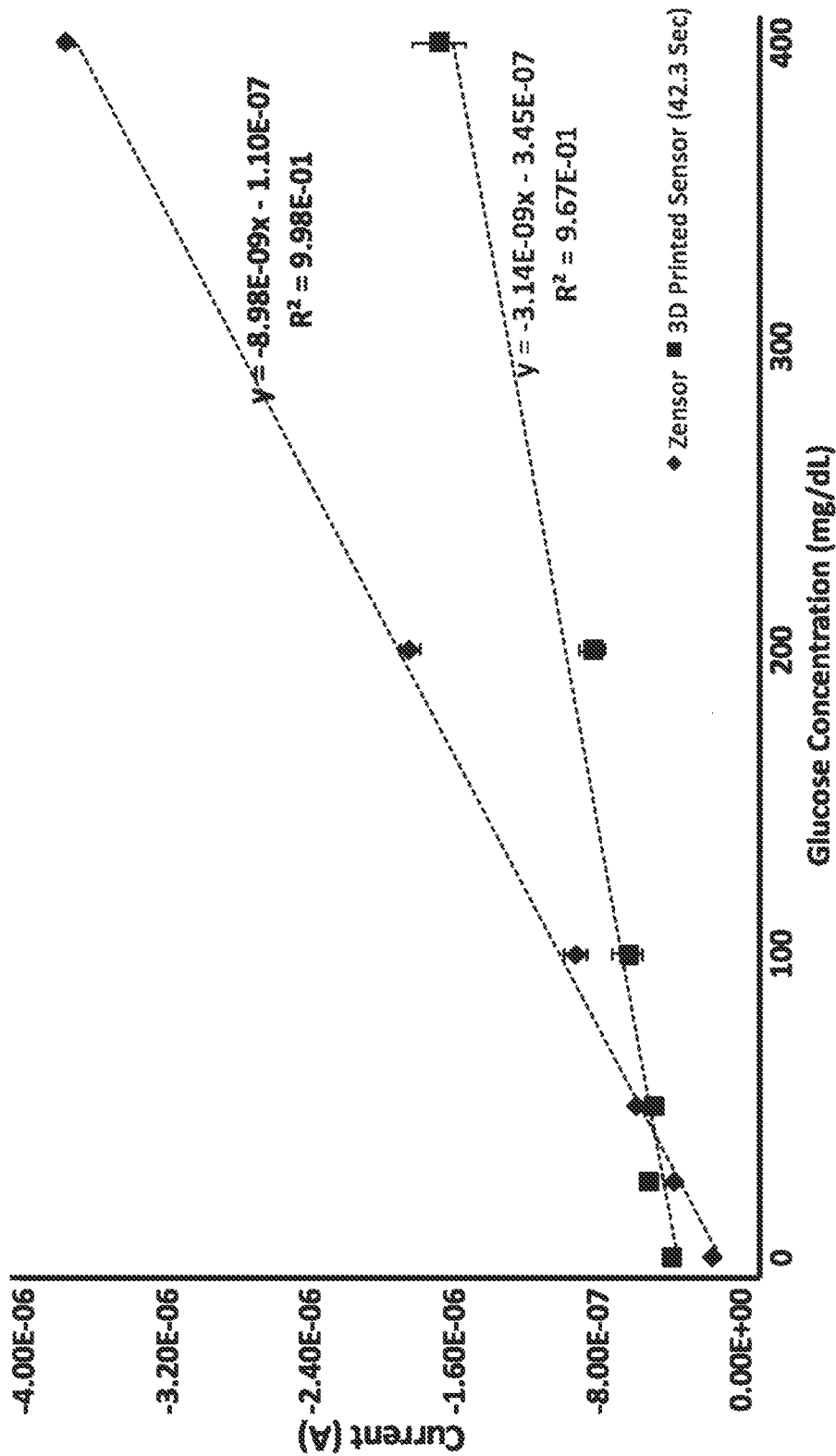
FIG. 37 is a representation of a 3D printed strip sensor calibration curve with glucose solutions based off current readings at 42.3 seconds (N=4) alongside a ZENSOR® sensor calibration curve.

The calibration curves for the three times were compared to the ZENSOR® calibration curve, as shown in FIGS. 36 to 38. FIG. 36 is a plot of current versus glucose solution concentration for a 3D-printed sensor based on readings at 3 seconds, 13 seconds, and 42.3 seconds, with comparison to a ZENSOR® sensor. The calibration curve for the current output time of 42.3 seconds is the most comparable to the calibration curve for the ZENSOR® sensor. This data suggests that the 3D-printed sensor could accurately detect glucose solution concentrations between 0 mg/dL and 400 mg/dL. FIG. 37 is a representation of the 3D printed strip sensor calibration curve with glucose solutions based off current readings at 42.3 seconds (N=4) alongside the ZENSOR® sensor calibration curve. FIG. 38 is a normal probability plot of standardized residual versus predicted current value for glucose concentrations at time of 42.3 seconds. There is no obvious pattern, which is evident of a good model.

It should be noted that due to using GDH-FAD, enhanced detection was possible. GDH-FAD is 25 times more enzymatic than glucose oxidase, which allows for faster and more accurate glucose detection. This could be a reason why the slope and R-squared at 42.3 seconds, shown previously herein, was the most optimal. However, like most commercially available sensors, an accurate glucose reading occurs almost instantaneously, and it is evident that detection of glucose at 13 seconds (e.g., in FIG. 31) showed equally good slope and correlation.

Exemplary Reactions in Glucose Monitoring Biosensor

Set out below are three reactions (1) to (3) that occur in a glucose monitoring sensor according to one exemplary embodiment.

$$\text{Glucose} + \text{GDH-FAD} \rightarrow \text{Glucono-1,5-lactone} + \text{GDH-FADH}_2 \quad \text{(Reaction 1)}$$

$$\text{GDH-FADH}_2 + [\text{Fe(CN)}_6]^{3-} \rightarrow \text{GDH-FAD} + [\text{Fe(CN)}_6]^{4-} \quad \text{(Reaction 2)}$$

$$[\text{Fe(CN)}_6]^{4-} + \text{Sensor} \rightarrow [\text{Fe(CN)}_6]^{3-} + \text{Sensor (reduced)} \quad \text{(Reaction 3)}$$

In reaction (1), the glucose reacts with the GDH-FAD enzyme. In this reaction, the glucose is oxidized and the GDH-FAD enzyme is reduced. In reaction (2), the reduced GDH-FAD enzyme from reaction (1) then reacts with the redox mediator, which is potassium ferricyanide ($[\text{Fe(CN)}_6]^{3-}$). The GDH-FAD enzyme is oxidized back to its original form, while the redox mediator is reduced. In reaction (3), the redox mediator reacts with the surface of the electrode. The reduced redox mediator is oxidized to its original form while the sensor is reduced.

The three reactions show the movement of electrons. The electron is passed from the glucose molecule, to the enzyme, to the redox mediator, and then finally to the sensor. The electron is then allowed to move through the electrode where the current is measured. The current is proportional to the concentration of glucose molecules, and can be utilized for monitoring glucose levels.

Verification of Operability of 3D-Printed Sensor by Amperometric i-t Testing

This disclosure represents the first known work in developing a 3D-printed glucose monitoring sensor, and verifying that it is possible to 3D-print a glucose monitoring sensor. Gamma prototype 3D printed sensors were determined to be sensitive to glucose concentrations between 0 mg/dL to 400 mg/dL, which is a large enough range to properly manage diabetes. The results showed that there were minimal differences between the current output at various glucose solution concentrations between the industry standard ZENSOR® and the 3D-printed graphene electrode. This showed that the 3D-printed sensor was responsive and sensitive. It was also determined that a 3D printed glucose monitoring device may be printed at a lower cost than currently available devices. As seen in FIG. 39, the cost of manufacturing the sensor was determined to be $0.40; however, this low cost for each sensor does not include the high initial cost of a 3D printer. 3D printers are continuing to become more affordable, so it is reasonable to predict that in the future they will be a common household appliance. This would allow diabetics to print their own test strips at home for much less than SMBG test strips. This would provide diabetics with a cost effective, accurate device that could reduce noncompliance issues due to the high cost of the test strips, ultimately improving their health outcomes.

3D printed sensing devices disclosed herein could potentially prevent the serious complications caused by diabetes for millions of individuals around the world. Providing diabetics with sensing devices disclosed herein may not only improve their health outcomes, but also drive down the cost of other devices on the market. This technology also could be utilized in developing countries, as local clinics could be supplied with a 3D-printer and filament as well as training on how to use such materials. This would provide the clinics with the necessary testing supplies for managing and monitoring diabetes.

It is to be appreciated that sensing devices disclosed herein are not necessarily limited to sensing of glucose. The present disclosure could be applied to sensors comprising other biomarkers, including biomarkers for pregnancy, cancer, and various diseases, which could be monitored using a 3D-printed sensor. This could allow hospitals to print sensors as needed, which could reduce wasted resources. The SMBG industry could also transition from screen-printed electrodes to 3D-printed electrodes, which could lower the cost of SMBG test strips.

In certain embodiments, filaments useable with a 3D printing apparatus may contain one or more chemical reagents. This would eliminate the need for reagents to be applied after printing. In certain embodiments, enzymes may be omitted, since high working (e.g., extrusion) temperatures used in 3D printers may tend to denature at least certain enzymes. In other embodiments, enzymes with a high heat tolerance or a different chemical such as Prussian blue could be incorporated in a 3D printing filament to enable enzymes to be 3D printed in, on, or over electrode leads.

The simplicity of 3D printed sensors offers support of a better and potentially easier method for glucose management. Additionally, the further optimization of 3D printed glucose sensors will ideally address aspects of World Health Organization standards of affordable, specific, sensitive, user-friendly, reliable, equipment-free, and deliverable biosensors. While efforts are still needed to best optimize such a design, a 3D printed glucose sensor has the potential to become a transformative method of glycemic management.

Upon reading the following description in light of the accompanying drawing figures, those skilled in the art will understand the concepts of the disclosure and will recognize applications of these concepts not particularly addressed herein. Those skilled in the art will recognize improvements and modifications to the preferred embodiments of the present disclosure. All such improvements and modifications are considered within the scope of the concepts disclosed herein and the claims that follow.

What is claimed is:

1. A blood glucose sensing device comprising:
   a substrate;
   a plurality of three-dimensionally printed electrode leads comprising graphene and a thermoplastic material arranged on or over the substrate, wherein each three-dimensionally printed electrode lead of the plurality of three-dimensionally printed electrode leads comprises a plurality of fused dots, rods, and/or layers; and
   glucose monitoring chemistry arranged in or on at least one three-dimensionally printed electrode lead of the plurality of three-dimensionally printed electrode leads.

2. The blood glucose sensing device of claim 1, wherein the glucose monitoring chemistry is adsorbed in the at least one three-dimensionally printed electrode lead of the plurality of three-dimensionally printed electrode leads.

3. The blood glucose sensing device of claim 1, wherein the thermoplastic material comprises an aliphatic polyester.

4. The blood glucose sensing device of claim 1, wherein the substrate comprises a polymer film.

5. The blood glucose sensing device of claim 4, wherein the polymer film comprises polyester terephthalate.

6. The blood glucose sensing device of claim 1, wherein the glucose monitoring chemistry comprises at least one enzyme.

7. The blood glucose sensing device of claim 6, wherein the at least one enzyme comprises glucose oxidase.

8. The blood glucose sensing device of claim 6, wherein the at least one enzyme comprises glucose-1-dehydrogenase.

9. The blood glucose sensing device of claim 6, wherein the at least one enzyme comprises a peroxidase.

10. The blood glucose sensing device of claim 1, wherein the glucose monitoring chemistry comprises oxygen as a final electron acceptor.

11. The blood glucose sensing device of claim 1, wherein the glucose monitoring chemistry comprises a redox mediator.

12. The blood glucose sensing device of claim 1, wherein the glucose monitoring chemistry is configured for direct electron transfer between an enzyme and at least one three-dimensionally printed electrode lead without a redox mediator.

13. The blood glucose sensing device of claim 1, wherein the plurality of three-dimensionally printed electrode leads comprises a reference electrode lead, a counter electrode lead, and a working electrode lead.

14. The blood glucose sensing device of claim 13, wherein the counter electrode lead is longer than each of the working electrode lead and the reference electrode lead.

15. The blood glucose sensing device of claim 13, wherein an end portion of the counter electrode lead partially surrounds an end portion of the working electrode lead.

16. The blood glucose sensing device of claim 13, wherein the working electrode lead comprises a resistivity of less than 1000Ω.

17. A method for fabricating at least one blood glucose sensing device, the method comprising:
    three-dimensionally printing a plurality of three-dimensionally printed electrode leads comprising graphene and a thermoplastic material arranged on or over a substrate, wherein each three-dimensionally printed electrode lead of the plurality of three-dimensionally printed electrode leads comprises a plurality of fused dots, rods, and/or layers; and
    providing glucose monitoring chemistry in or on at least one three-dimensionally printed electrode lead of the plurality of three-dimensionally printed electrode leads.

18. The method of claim 17, wherein said providing of glucose monitoring chemistry in or on the at least one three-dimensionally printed electrode lead comprises soaking the at least one three-dimensionally printed electrode lead in an enzyme solution.

19. The method of claim 17, wherein said providing of glucose monitoring chemistry in or on the at least one three-dimensionally printed electrode lead comprises depositing at least one enzyme concurrently with the three-dimensional printing of the at least one three-dimensionally printed electrode lead of the plurality of three-dimensionally printed electrode leads.

20. The method of claim 17, wherein the at least one blood glucose sensing device comprises the substrate.

21. The method of claim 17, wherein the plurality of three-dimensionally printed electrode leads comprises a reference electrode lead, a counter electrode lead, and a working electrode lead.

22. The method of claim 17, wherein the plurality of three-dimensionally printed electrode leads comprises a plurality of reference electrode leads, a plurality of counter electrode leads, and a plurality of working electrode leads, and the method further comprises separating the substrate into a plurality of glucose sensing devices each including a reference electrode lead, a counter electrode lead, and a working electrode lead.

23. The method of claim 17, wherein the thermoplastic material comprises an aliphatic polyester.

24. The method of claim 17, wherein the three-dimensional printing of the plurality of three-dimensionally printed electrode leads comprises dispensing, from an extruder head, molten filament material comprising the graphene and the thermoplastic material.

25. The method of claim 24, wherein further comprising effectuating travel between the extruder head and the substrate during the three-dimensional printing.

\* \* \* \* \*